(12) United States Patent
Yamazaki et al.

(10) Patent No.: US 9,008,377 B2
(45) Date of Patent: *Apr. 14, 2015

(54) SYSTEM AND METHOD FOR IDENTIFYING AN INDIVIDUAL

(71) Applicant: Semiconductor Energy Laboratory Co., Ltd., Atsugi-shi, Kanagawa-ken (JP)

(72) Inventors: Shunpei Yamazaki, Tokyo (JP); Jun Koyama, Kanagawa (JP); Yu Yamazaki, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/339,510

(22) Filed: Jul. 24, 2014

(65) Prior Publication Data

US 2014/0334695 A1 Nov. 13, 2014

Related U.S. Application Data

(63) Continuation of application No. 13/865,413, filed on Apr. 18, 2013, now Pat. No. 8,805,032, which is a continuation of application No. 12/652,341, filed on Jan. 5, 2010, now Pat. No. 8,437,510, which is a continuation of application No. 09/833,674, filed on Apr. 13, 2001, now Pat. No. 7,751,600.

(30) Foreign Application Priority Data

Apr. 18, 2000 (JP) ................................. 2000-116694

(51) Int. Cl.
*G06K 9/00* (2006.01)
*G06F 21/32* (2013.01)

(Continued)

(52) U.S. Cl.
CPC .............. *G06K 9/0002* (2013.01); *G06F 21/32* (2013.01); *G06Q 20/4014* (2013.01); *G07C 9/00158* (2013.01); *G06K 9/0004* (2013.01); *A61B 5/1172* (2013.01); *H04M 1/72522* (2013.01)

(58) Field of Classification Search
None
See application file for complete search history.

(56) References Cited

U.S. PATENT DOCUMENTS 3,581,282 A 5/1971 Altman
4,229,237 A 10/1980 Bensahel et al.
(Continued)

FOREIGN PATENT DOCUMENTS

DE 19809006 9/1999
DE 20008345 8/2000
(Continued)

OTHER PUBLICATIONS

Palm Pilot for Credit/Debit/Cash Card With Biometric Authentication, IBM Technical Disclosure Bulletin, May 1, 1999, vol. 42, No. 421.

(Continued)

*Primary Examiner* — Vikkram Bali
(74) *Attorney, Agent, or Firm* — Fish & Richardson P.C.

(57) ABSTRACT

The present invention provides a system for identifying an individual provided with a portable communication device. In a system for identifying an individual using a portable communication device with a display, the display is a sensor-incorporated display, the sensor-incorporated display reads the biological information of a user, and, based on the read information, identifies an individual.

18 Claims, 18 Drawing Sheets

(51) Int. Cl.
*G06Q 20/40* (2012.01)
*G07C 9/00* (2006.01)
*A61B 5/117* (2006.01)
*H04M 1/725* (2006.01)

(56) References Cited

U.S. PATENT DOCUMENTS

| | | | |
|---|---|---|---|
| 4,263,056 A | 4/1981 | Bensahel et al. | |
| 4,532,508 A | 7/1985 | Ruell | |
| 5,105,238 A | 4/1992 | Nikaido et al. | |
| 5,210,797 A | 5/1993 | Usui et al. | |
| 5,412,727 A | 5/1995 | Drexler et al. | |
| 5,420,936 A | 5/1995 | Fitzpatric et al. | |
| 5,446,290 A | 8/1995 | Fujieda et al. | |
| 5,528,355 A | 6/1996 | Maase et al. | |
| 5,550,066 A | 8/1996 | Tang et al. | |
| 5,574,293 A | 11/1996 | Arai et al. | |
| 5,627,364 A | 5/1997 | Codama et al. | |
| 5,719,950 A | 2/1998 | Osten et al. | |
| 5,929,845 A | 7/1999 | Wei et al. | |
| 5,930,804 A | 7/1999 | Yu et al. | |
| 6,021,212 A | 2/2000 | Ho | |
| 6,026,293 A | 2/2000 | Osborn | |
| 6,028,581 A | 2/2000 | Umeya | |
| 6,038,666 A | 3/2000 | Hsu et al. | |
| 6,040,810 A | 3/2000 | Nishimura | |
| 6,104,922 A | 8/2000 | Baumann | |
| 6,141,436 A | 10/2000 | Srey et al. | |
| 6,144,756 A | 11/2000 | Takahashi et al. | |
| 6,175,922 B1 | 1/2001 | Wang | |
| 6,182,221 B1 | 1/2001 | Hsu et al. | |
| 6,219,793 B1 | 4/2001 | Li et al. | |
| 6,236,063 B1 | 5/2001 | Yamazaki et al. | |
| 6,243,155 B1 | 6/2001 | Zhang et al. | |
| 6,274,887 B1 | 8/2001 | Yamazaki et al. | |
| 6,327,376 B1 | 12/2001 | Harkin | |
| 6,370,263 B1 | 4/2002 | Hiratsuka et al. | |
| 6,445,932 B1 | 9/2002 | Soini et al. | |
| 6,480,305 B1 | 11/2002 | Resman | |
| 6,490,366 B1 | 12/2002 | Haneda et al. | |
| 6,547,130 B1 | 4/2003 | Shen | |
| 6,580,094 B1 | 6/2003 | Yamazaki et al. | |
| 6,583,439 B2 | 6/2003 | Yamazaki et al. | |
| 6,594,505 B1 | 7/2003 | Ishii | |
| 6,628,810 B1 | 9/2003 | Harkin | |
| 6,657,538 B1 | 12/2003 | Ritter | |
| 6,747,638 B2 | 6/2004 | Yamazaki et al. | |
| 6,751,734 B1 | 6/2004 | Uchida | |
| 6,809,343 B2 | 10/2004 | Yamazaki et al. | |
| 6,815,654 B1 | 11/2004 | Fujieda et al. | |
| 7,180,092 B2 | 2/2007 | Yamazaki et al. | |
| 7,279,752 B2 | 10/2007 | Yamazaki et al. | |
| 7,402,467 B1 | 7/2008 | Kadono et al. | |
| 7,473,928 B1 | 1/2009 | Yamazaki et al. | |
| 7,521,722 B2 | 4/2009 | Yamazaki et al. | |
| 7,548,023 B2 | 6/2009 | Yamazaki et al. | |
| 7,751,600 B2 | 7/2010 | Yamazaki et al. | |
| 7,989,812 B2 | 8/2011 | Yamazaki et al. | |
| 8,017,945 B2 | 9/2011 | Yamazaki et al. | |
| 8,133,748 B2 | 3/2012 | Yamazaki et al. | |
| 8,437,510 B2 | 5/2013 | Yamazaki et al. | |
| 8,805,032 B2 * | 8/2014 | Yamazaki et al. | 382/124 |
| 2001/0030704 A1 | 10/2001 | Kimura | |
| 2001/0047479 A1 | 11/2001 | Bromba et al. | |
| 2002/0011972 A1 | 1/2002 | Yamazaki et al. | |
| 2002/0034930 A1 | 3/2002 | Yamazaki et al. | |
| 2007/0146333 A1 | 6/2007 | Yamazaki | |
| 2009/0109143 A1 | 4/2009 | Yamazaki et al. | |
| 2012/0056190 A1 | 3/2012 | Yamazaki et al. | |
| 2012/0061718 A1 | 3/2012 | Yamazaki et al. | |

FOREIGN PATENT DOCUMENTS

| | | |
|---|---|---|
| EP | 0426423 A | 5/1991 |
| EP | 0593386 A | 4/1994 |
| EP | 0855666 A | 7/1998 |
| EP | 0924657 A | 6/1999 |
| JP | 62-204390 A | 9/1987 |
| JP | 03-142685 A | 6/1991 |
| JP | 07-271981 A | 10/1995 |
| JP | 08-185519 A | 7/1996 |
| JP | 10-262951 A | 10/1998 |
| JP | 11-065763 A | 3/1999 |
| JP | 11-316818 A | 11/1999 |
| JP | 11-326954 A | 11/1999 |
| JP | 11-345264 A | 12/1999 |
| JP | 2000-276445 A | 10/2000 |
| JP | 2001-005945 A | 1/2001 |
| JP | 4693217 | 6/2011 |
| JP | 4693222 | 6/2011 |
| WO | WO-98/11750 | 3/1998 |
| WO | WO-98/40962 | 9/1998 |
| WO | WO-99/18590 | 4/1999 |
| WO | WO-99/24938 | 5/1999 |
| WO | WO-99/28701 | 6/1999 |
| WO | WO-00/17823 | 3/2000 |
| WO | WO-00/63769 | 10/2000 |

OTHER PUBLICATIONS

Office Action (Application No. 01109595.7) Dated Jun. 29, 2007.
Search Report (Application No. 01109595.7) Dated Mar. 23, 2004.

* cited by examiner

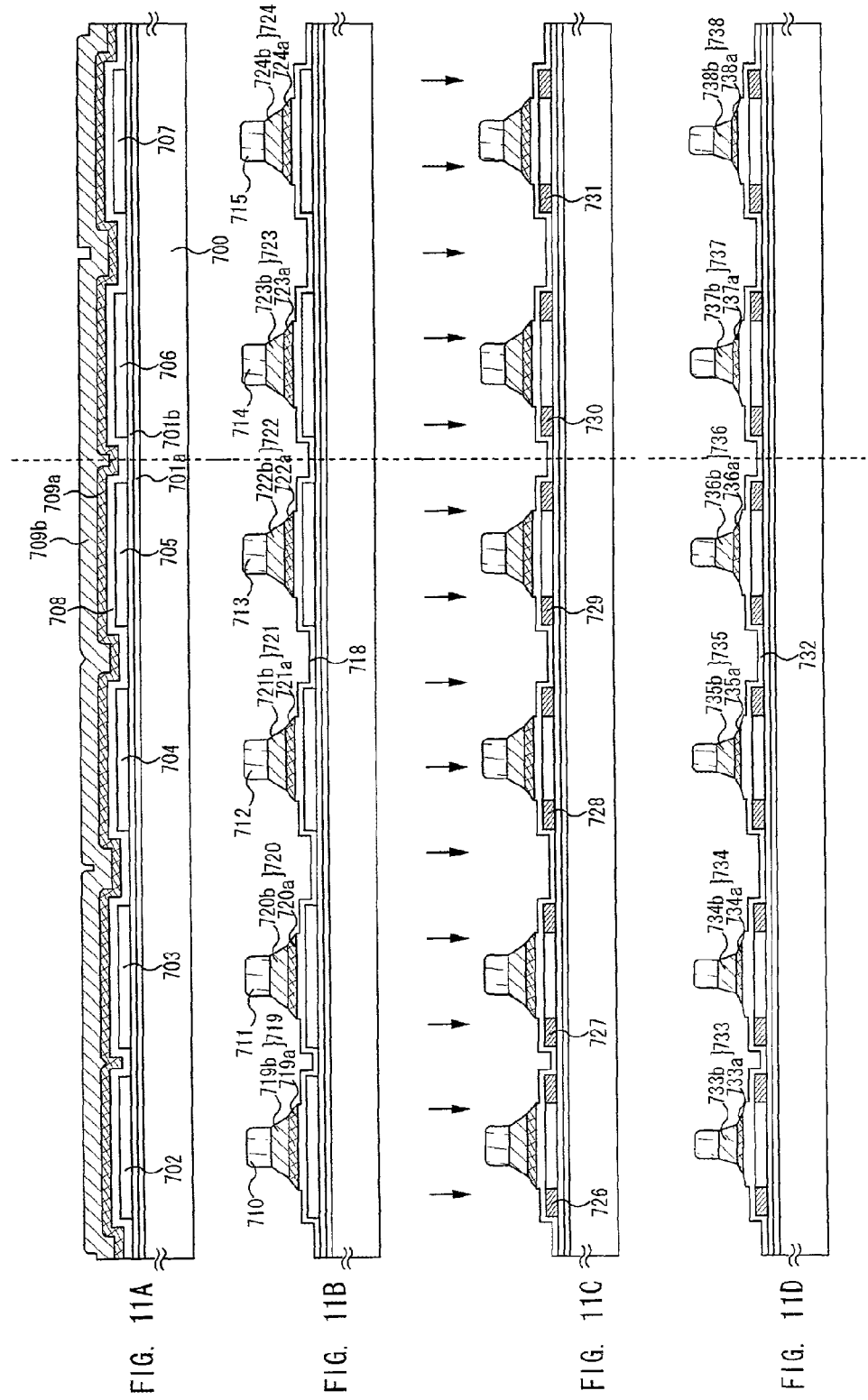

SYSTEM AND METHOD FOR IDENTIFYING AN INDIVIDUAL

CROSS-REFERENCE TO RELATED APPLICATIONS

This application is a continuation of U.S. application Ser. No. 13/865,413, filed Apr. 18, 2013, now allowed, which is a continuation of U.S. application Ser. No. 12/652,341, filed Jan. 5, 2010, now U.S. Pat. No. 8,437,510, which is a continuation of U.S. application Ser. No. 09/833,674, filed Apr. 13, 2001, now U.S. Pat. No. 7,751,600, which claims the benefit of a foreign priority application filed in Japan as Serial No. 2000-116694 on Apr. 18, 2000, all of which are incorporated by reference.

BACKGROUND OF THE INVENTION

1. Field of the Invention

This invention relates to a system for identifying an individual or a method for identifying the same, in particular, a system or a method for identifying an individual by means of a display, which is provided with a sensor.

2. Description of the Related Art

In recent years, the communication technology through the Internet by means of portable communication device, such as a portable telephone or a portable information terminal, are developing rapidly. The conventional Internet assures communication through a telephone line to which a personal computer installed in an office or a house is connected. However, recently, the i-mode that permits of utilization of the Internet easily through a portable telephone became popular and various exchanges of information became simple to carry out.

What is going to be described in this specification relates to a system for identifying an individual by means of the Internet and a portable communication device.

FIG. 16 shows an example of conventional portable telephone apparatus. A conventional telephone apparatus shown in FIG. 16 is comprised of a main body 2601, a voice output part 2602, a voice input part 2603, a display 2604, operation switch 2605, an antenna 2606, etc. In case of an ordinary telephone call, the phone number of the opposite end, the state of reception of radio wave, etc. are shown on the liquid crystal display. And, in the case where the Internet is utilized, the necessary information concerning the opposite end are to be displayed.

When receiving or giving money on the Internet by means of a conventional portable telephone as shown in FIG. 16, identification on the person was necessary. In this case, the confirmation has been executed by entering the personal identification number, which had been registered beforehand on the opposite end, and by exchanging data with the opposite end.

FIG. 17 shows the conventional identification flow of an individual. At first, the user makes a connection through the Internet with the opposite end, then enters the numerical value for identification (PIN) under the condition specified by the opposite end. The opposite end which has received the numerical value checks it with the numerical value registered beforehand and confirms whether or not they coincide. If they coincide here, the user is confirmed and becomes capable to obtain the desired reception.

As explained above, the following problems exist in the conventional identifying system using a portable telephone:

1. Confirmation of individual is difficult. In the case where the personal identification number is leaked to another person, there is a possibility of an abuse.
2. Confirmation of an individual is executed for each communication with the opposite end, so that the communication cost increases and a reconfirmation becomes necessary if the phone call is cut during the conversation.
3. Many keyboard operations.

SUMMARY OF THE INVENTION

The present invention provides a system for identifying an individual comprising: a means for reading the biological information of a user by means of a sensor-incorporated display; a means for checking the read biological information with the reference biological information; and a means for transmitting information to the destination of communication that the checking has matched in the case where they have matched.

The present invention provides a system for identifying an individual, s comprising: a means for reading the biological information of a user by means of a sensor-incorporated display; a means for checking the read biological information with the reference biological information; a means for transmitting information to the destination of communication that the checking has matched in the case where they have matched; and a means for notifying said user, after said destination of communication receives information that said checking has matched, that the communication between said user and said destination of communication has been authorized.

The present invention provides a system for identifying an individual, which is provided with a portable communication device having a sensor-incorporated display, comprising: a means for reading the biological information of a user by means of said sensor-incorporated display; a means for checking the read biological information with the reference biological information stored in said portable communication device; and a means for transmitting information to the destination of communication that the checking has matched in the case where they have matched.

The present invention provides a system for identifying an individual, which is provided with a portable communication device having a sensor-incorporated display, comprising: a means for reading the biological information of a user by means of a sensor-incorporated display; a means for checking the read biological information with the reference biological information stored in said sensor-incorporated display; a means for transmitting information to the destination of communication that they have matched in the case where said checking has matched; and a means for transmitting information to said portable communication device, after the destination of communication receives information that said checking has matched, that the communication between said user and said destination of communication has been authorized.

The present invention provides a method for identifying an individual, comprising: a means for reading the biological information of a user by means of a sensor-incorporated display; a means for checking the read biological information with the reference biological information; and a means for transmitting information to the destination of communication that they have matched in the case where said checking has matched.

The present invention provides a method for identifying an individual, comprising: a means for reading the biological information of a user by means of a sensor-incorporated display; a means for checking the read biological information with the reference biological information; a means for transmitting information to the destination of communication that they have matched in the case where said checking has matched; and a means for notifying said user, after said destination of communication receives information that said checking has matched, that the communication between said user and said destination of communication has been authorized.

The present invention provides a method for identifying an individual, which is provided with a portable communication device having a sensor-incorporated display, comprising: a means for reading the biological information of a user by means of said sensor-incorporated display; a means for checking the read biological information with the reference biological information stored in said portable communication device; and a means for transmitting information to the destination of communication that they have matched in the case where said checking has matched.

The present invention provides a method for identifying an individual, which is provided with a portable communication device having a sensor-incorporated display, comprising: a means for reading the biological information of a user by means of said sensor-incorporated display; a means for checking the read biological information with the reference biological information stored in said portable communication device; a means for transmitting information to the destination of communication that they have matched in the case where said checking has matched; and a means for transmitting information to the portable communication device, after the destination of communication receives information that said checking has matched, that the communication between said user and said destination of communication has been authorized.

The portable communication device of this invention is possible to identify an individual by means of the functions of the sensor incorporated in the device and has a possibility to have a high reliability and simplicity, compared with the conventional identification works consisting of entering a numerical value (personal identification number).

BRIEF DESCRIPTION OF THE DRAWINGS

FIGS. 11A to 11D are drawings showing the fabrication process of the sensor-incorporated display.

DETAILED DESCRIPTION OF THE PREFERRED EMBODIMENTS

In this invention, as an embodiment to resolve the problems described above, a biological information that a user has (a specific physical information that the person has naturally such as finger prints or palm pattern), instead of personal identification number, is utilized for identification of an individual. And by doing the identification process not on the opposite end, but by the portable communication device itself, the simplicity as a system is increased.

Figure 1:
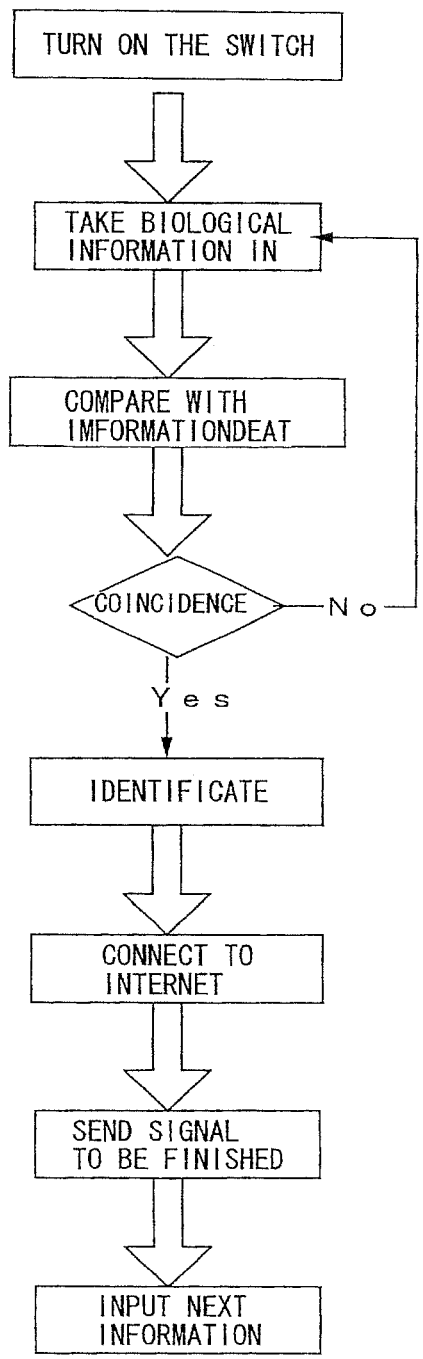
FIG. 1 is an identification flow of the system for identifying an individual of this invention.

FIG. 1 shows the identification flow of the system of identifying an individual of this invention. At first, collection of biological information is instructed by means of a keyboard. If programmed beforehand, it is easy to make it possible to start the collection of biological information by pushing only on one key. Furthermore, it is also possible to set up to start automatically the collection of biological information when the portable communication device is switched on.

The obtained biological information is compared with the person's reference biological information, which is stored in the non-volatile memory of the portable communication device. If it is then judged that the read biological information coincides with the reference biological information, the user is judged as the legitimate owner of the portable communication device. The transmission to the opposite end is carried out after finishing the judgement. At this time, the identification process has already been finished, there is no need to effectuate again the identification process on the opposite end, and the opposite end needs only to receive information from the portable communication device that the identification has been finished.

What differentiates the portable communication device, which is used in the system for identifying an individual of the embodiment of the present invention, from conventional ones is that the display of the system for identifying in the embodiment of the present invention has a built-in sensor, while the display of conventional portable telephones is dedicated to displaying. The sensor used here is an area sensor which is utilized to read the biological information of a user. Biological information means physically inherent information that the user has naturally, such as a fingerprint or a palm pattern (the lines on the palm).

Figure 2:
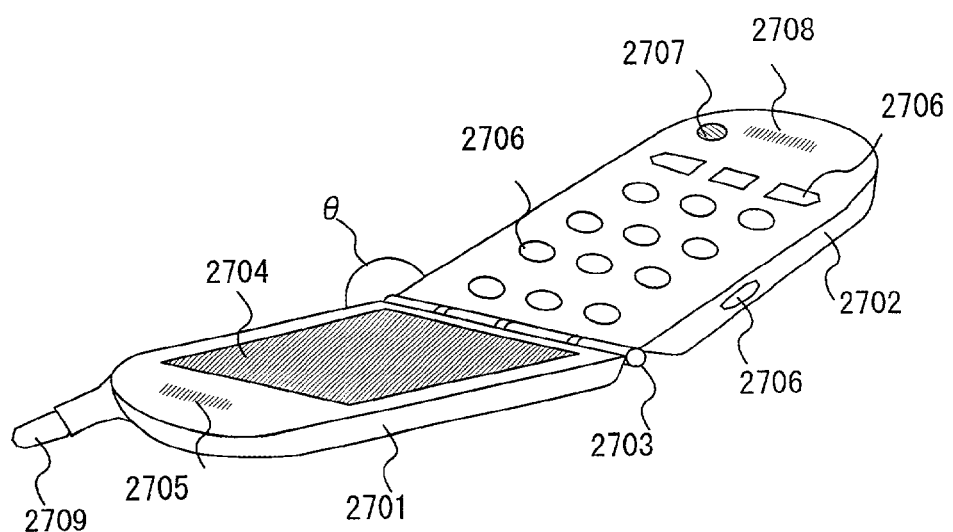
FIG. 2 is an external view of the portable communication device of this invention.

Then, description is given of the portable communication device of this invention. FIG. 2 shows a portable communication of this invention with a display panel 2701 and an operation panel 2702. The display panel 2701 and the operation panel 2702 are connected at the connecting part 2703. And at the connecting part 2703, the angle q between the surface on which is installed the sensor-incorporated display 2704 (display with a built-in sensor) of display panel 2701 and the surface on which is installed the operating keys 2706 of operation panel 2702 is able to be changed to be any degrees.

The display panel 2701 has a sensor-incorporated display 2704. Furthermore, the portable communication device shown in FIG. 2 has a function of a telephone, the display panel 2701 has a voice output part 2705, and the voice is output from the voice output part 2705. For the sensor-incorporated display 2704, an EL display is used.

The operation panel 2702 has operating keys 2706, a power supply switch 2707 and a voice input part 2708. Furthermore, although in FIG. 2 the operating keys 2706 and the power supply switch 2707 are provided separately, a structure in which the power supply switch 2707 is included in the operating keys 2706 may be employed. Voice is input at the voice input part 2708.

Furthermore, although in FIG. 2 the display panel 2701 has a voice output part 2705 and the operation panel 2702 has a voice input part 2708, this embodiment is not limited to this structure. It is also possible that the display panel 2701 has a voice input part 2708 and the operation panel has a voice output part 2705. Furthermore, it is also possible that both the voice output part 2705 and the voice input part 2708 are installed on the display panel 2701 or that both are installed on the operation panel 2702.

Figure 3:
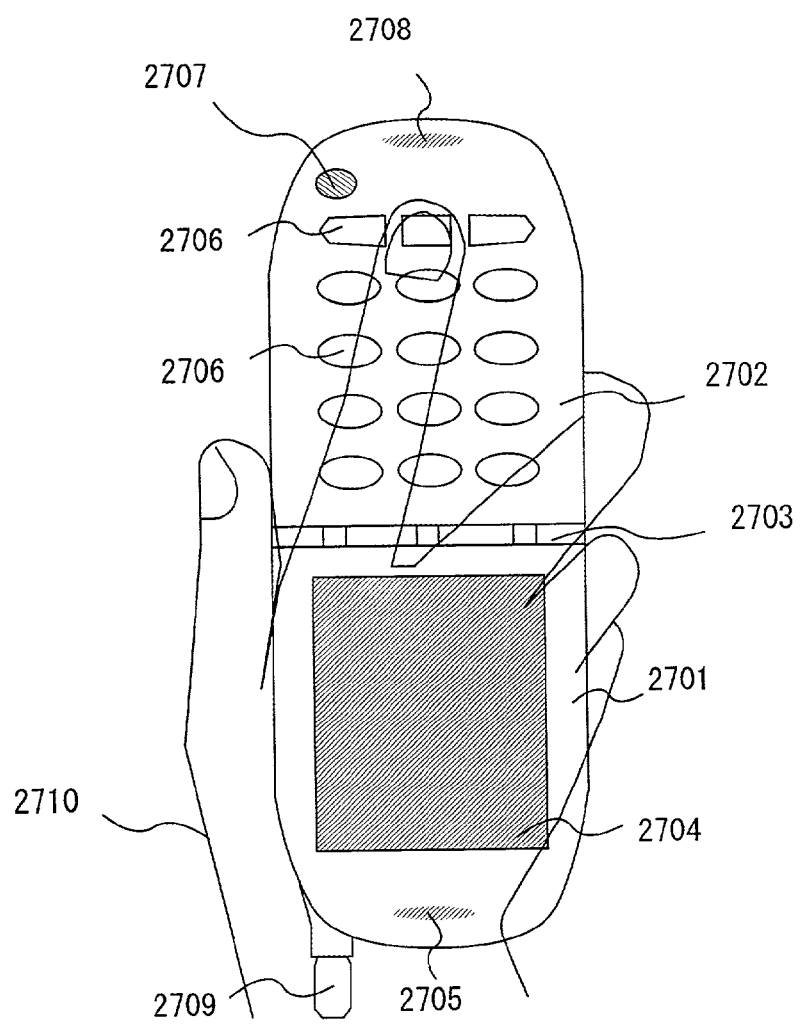
FIG. 3 is a drawing showing how to use the portable communication device of this invention.
Figure 4:
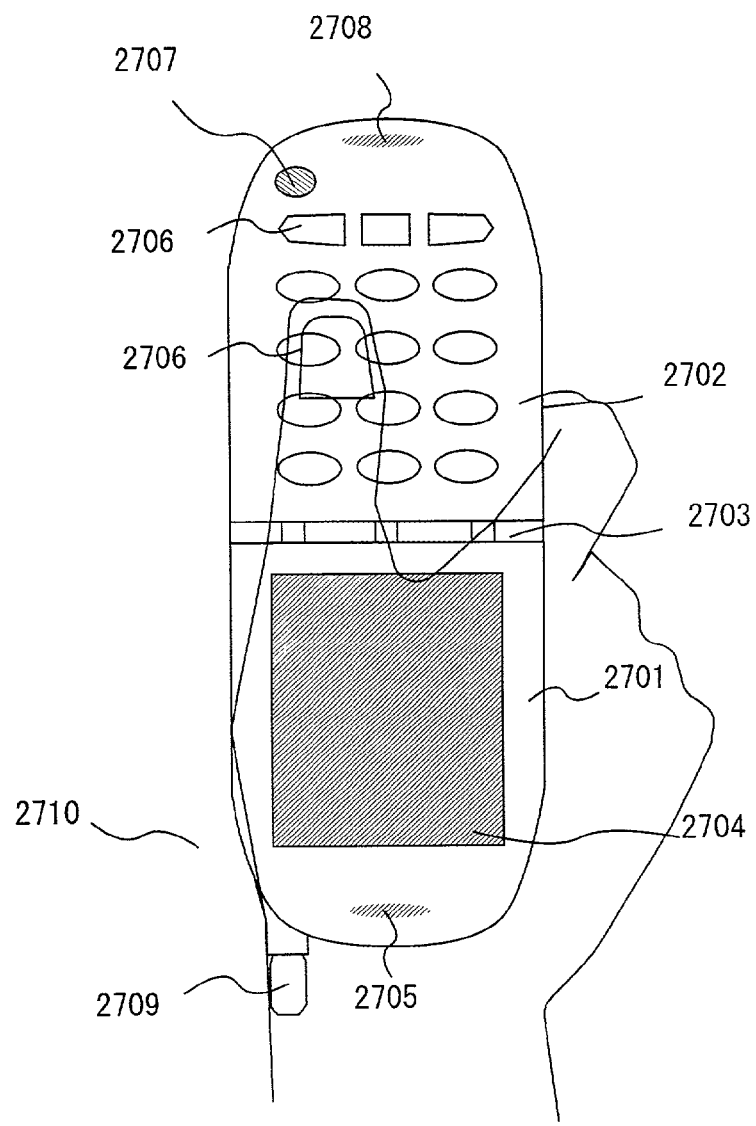
FIG. 4 is a drawing showing how to use the portable communication device of this invention.
Figure 18:
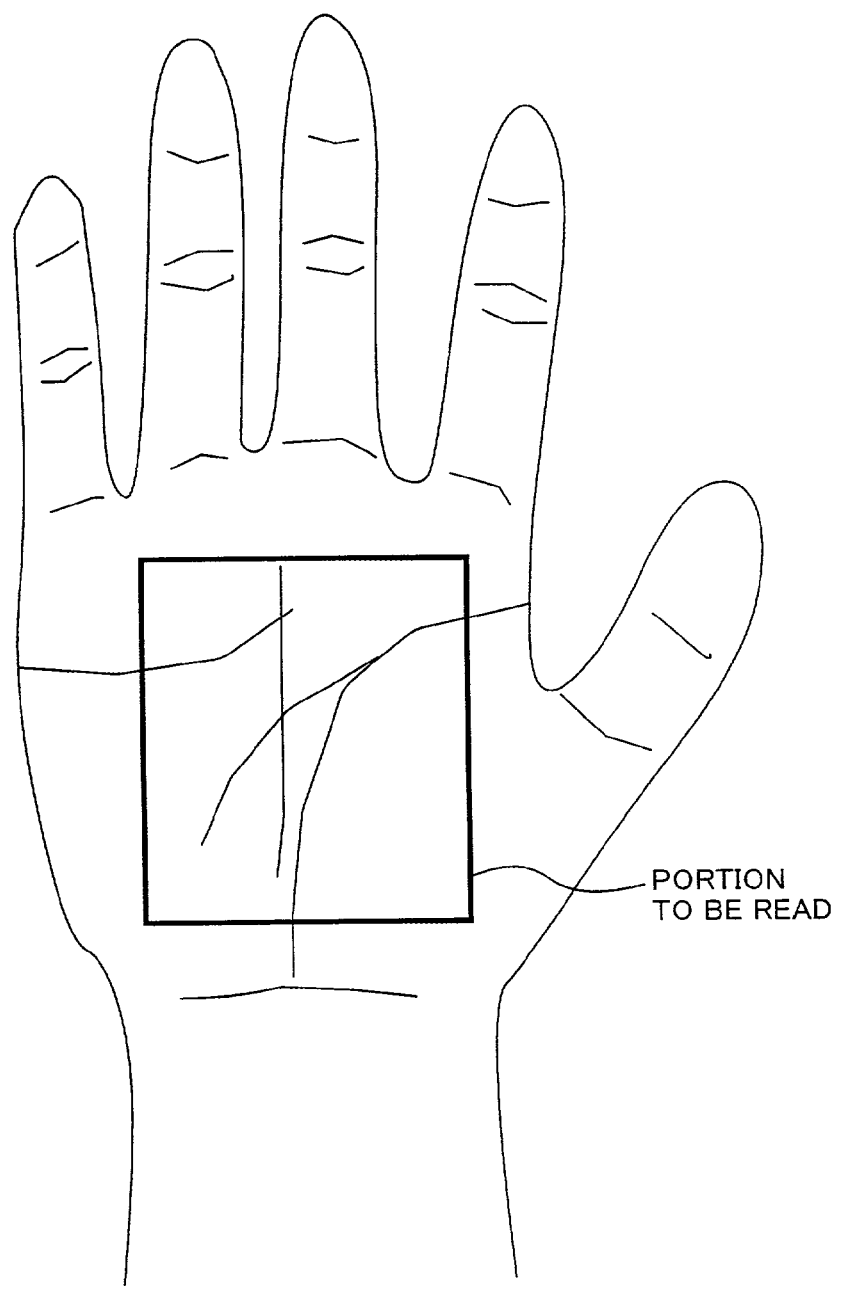
FIG. 18 is a drawing showing the position of the palm pattern to be read.

With reference to FIG. 3 and FIG. 4, how to use the portable communication device shown in FIG. 2 will be described. In case where the identification is executed by this device, it is used by posing the palm on the portable communication device to cover it. The identification is executed by key operation on the keyboard, while the sensor-incorporated display reads the palm of a user and does the identification process. Here, as the palm covers the portable device, the light used for sensing should be obtained from the interior of the display. In consequence, a spontaneous light emitting display is preferred such as an organic EL display. As shown in FIG. 18, the sensor reads the palm pattern (the lines on the palm).

Although, while FIG. 3 shows an example of operation of the operating keys 2706 with the index finger, it is also possible to operate the operating keys 2706 with the thumb as shown in FIG. 4. Furthermore, the operating keys 2706 can be installed on the side surface of operation panel 2702. The operation can be executed either with the index finger or the thumb of one hand (the dominant hand).

The embodiments of this invention shall be described below.

[Embodiment 1]

In the following, the arrangement and action of the examples of portable communication device having a sensor-incorporated display used in this invention shall be described.

Figure 5:
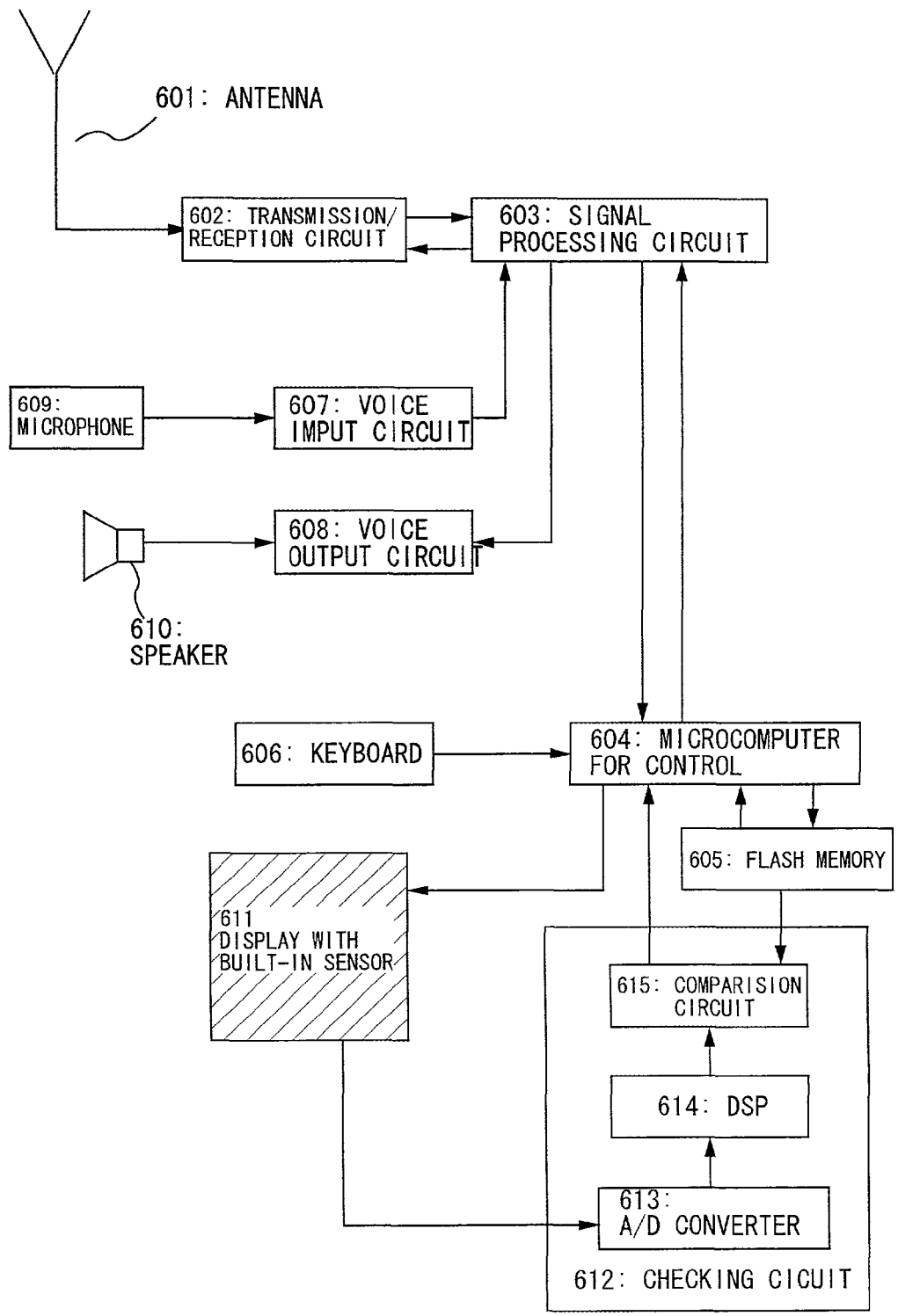
FIG. 5 is a block diagram showing the structure of the sensor-incorporated display.

FIG. 5 is a block diagram of the portable communication device of this embodiment. This portable communication device is identical with conventional ones in having an antenna 601, a transmission and reception circuit 602, a signal processing circuit 603 to compress, expand and encode signals, a microcomputer 604 for control, a flash memory 605, a keyboard 606, a voice input circuit 607, voice output circuit 608, a microphone 609, a speaker 610 and, in addition, this device further has a sensor-incorporated display 611, a checking circuit part 612, etc.

When doing a check, the analog image information obtained by the sensor in the display is converted to digital signals by means of the A/D converter 613. The converted signals are sent to DSP (digital signal processor) 614 and signal processing is carried out. In the signal processing, to make the distinguishing of the lines on the palm easier, the portions of the image at which the shade change can be made conspicuous by using a differential filter or the like. The data of the lines on the palm thus obtained are digitized inside DSP 614 and sent to the comparison circuit 615. At the comparison circuit 615, the reference data stored in flash memory 605 are also called and the two data are checked by comparison.

As methods for distinguishing the biological information, there is a method of checking the characteristics which compares and checks the characteristics respectively and a method of image matching which compares directly two data. Either of these methods can be used without problem. Furthermore, in stead of only one datum, several identification data, for example, by changing a little the direction of the hand, can be provided to make the identification more precise.

If the matching is observed here, the microcomputer 604 for control outputs an identification signal which is transmitted via signal processing part 603, transmission and reception circuit 602, and antenna 601, and then delivered through the Internet. etc.

[Embodiment 2]

Figure 6:
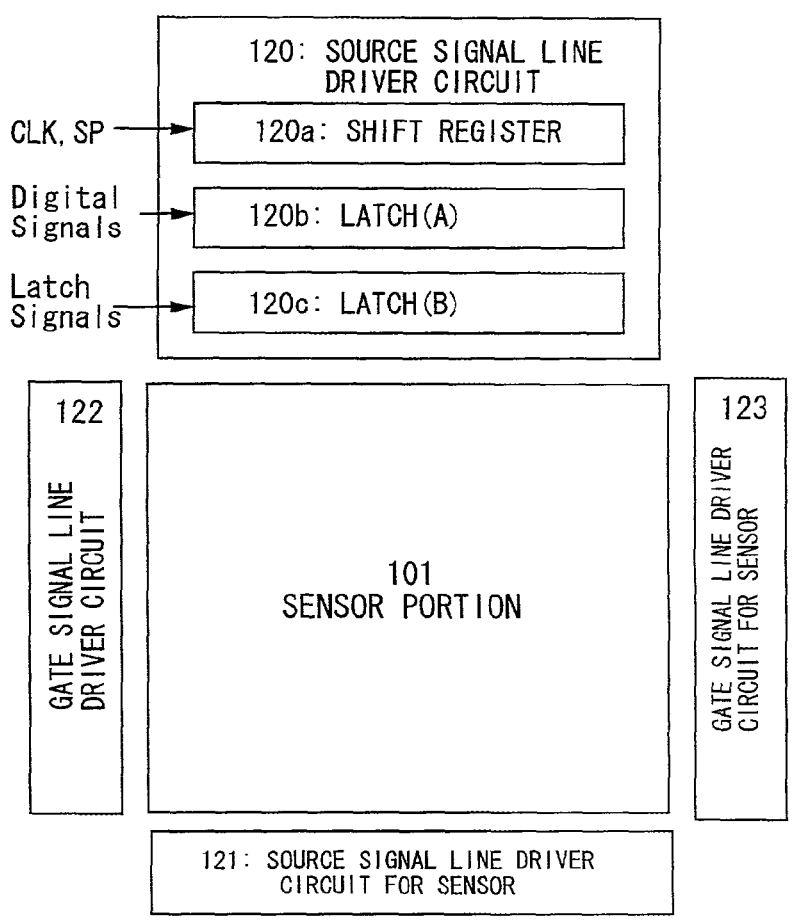
FIG. 6 is a block diagram showing the structure of the sensor-incorporated display.

FIG. 6 is a block diagram showing the structure of sensor-incorporated display used in this invention. 120 is a source signal line drive circuit and 122 is a gate signal line drive circuit, both control the driving of the TFT 104 for switching and the TFT 105 for driving EL. And 121 is a source signal line drive circuit for sensor and 123 is a gate signal line drive circuit for sensor, both control the driving of the TFT 110 for reset, the TFT 111 for buffer and TFT 112 for selection. Furthermore, in this description, the source signal line drive circuit 120, gate signal line drive circuit 122, source signal line drive circuit 121 for sensor, and gate signal line drive circuit 123 for sensor are called driving parts.

The source signal line drive circuit 120 has a shift register 120*a*, a latch (A) 120*b* and a latch (B) 120*c*. At the source signal line drive circuit 120, the clock signal (CLK) and the start pulse (SP) are entered to the shift register 120*a*. The shift register 120*a* generates timing signals in turn according to these clock signals (CLK) and start signals (SP) to provide in order the downstream circuits with timing signals.

Furthermore, it is possible to provide the downstream circuits with buffer amplified timing signals in order after having amplified the timing signal from the shift register 120*a* by a buffer (not shown) for example. Because on the wires where the timing signals are provided there are many circuits or elements connected, its load capacitance (parasitic capacitance) is large. The buffer is installed in order to avoid a "slow down" of rise up or rise down of the timing signals due to this large load capacitance.

Figure 7:
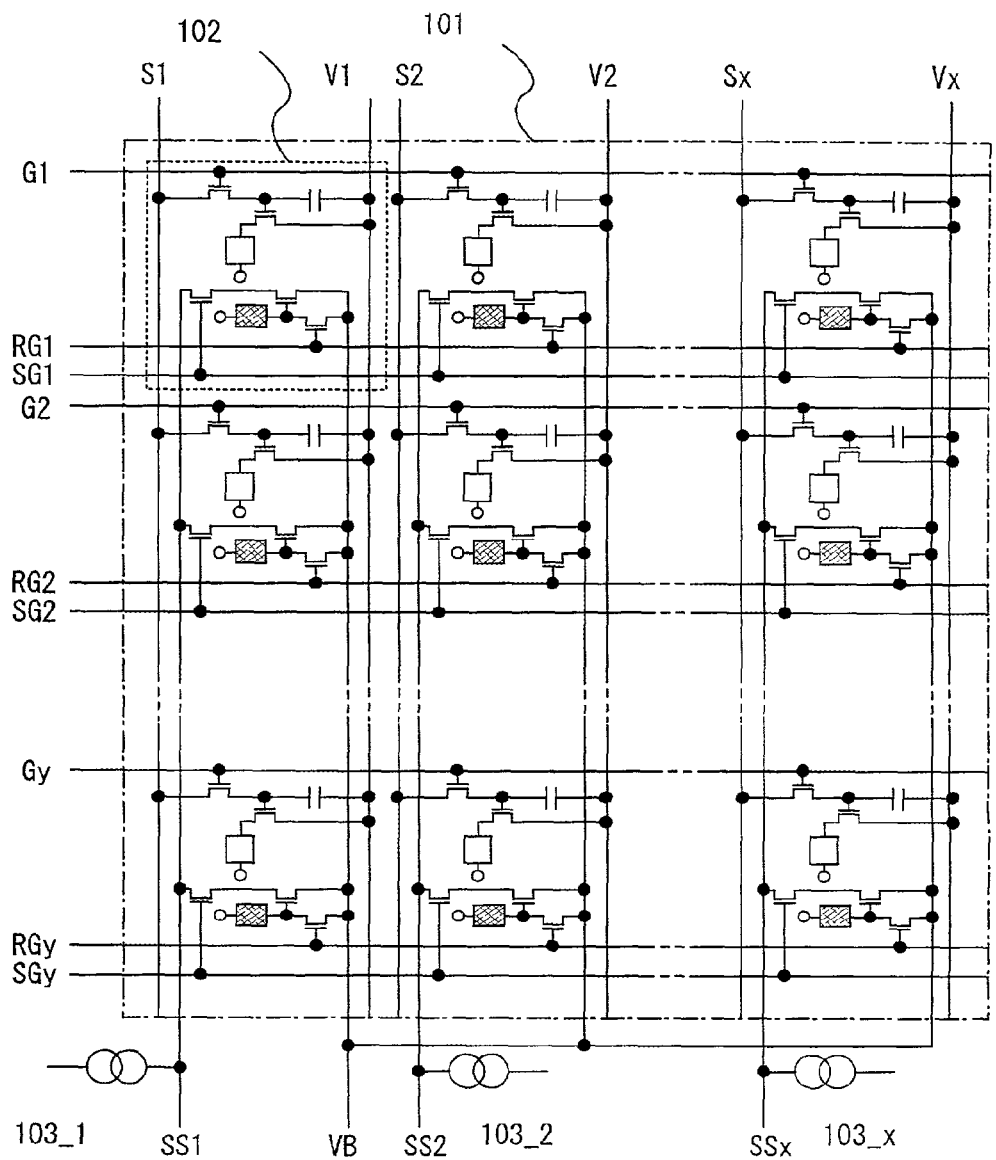
FIG. 7 is a circuit diagram of the sensor portion.

In FIG. 7 the circuit diagram of the sensor portion 101 is shown. The sensor portion 101 is provided with source signal lines S1 to Sx, power supply lines V1 to Vx, gate signal lines G1 to Gy, gate signal lines RG1 to RGy for reset, gate signal lines SG1 to SGy for sensor, output wires SS1 to SSx for sensor and power supply line VB for sensor.

The sensor portion 101 has a plurality of pixels 102. The pixel 102 has either one of source signal lines S1 to Sx, any one of power supply lines V1 to Vx, either one of gate signal lines G1 to Gy, either one of gate signal lines RG1 to RGy for reset, either one of gate signal lines SG1 to SGy for sensor, either one of sensor output wires SS1 to SSx and power supply line VB for sensor.

Each of the sensor output wires SS1 to SSx is connected respectively to the constant current sources 103_1 to 103_x.

Figure 8:
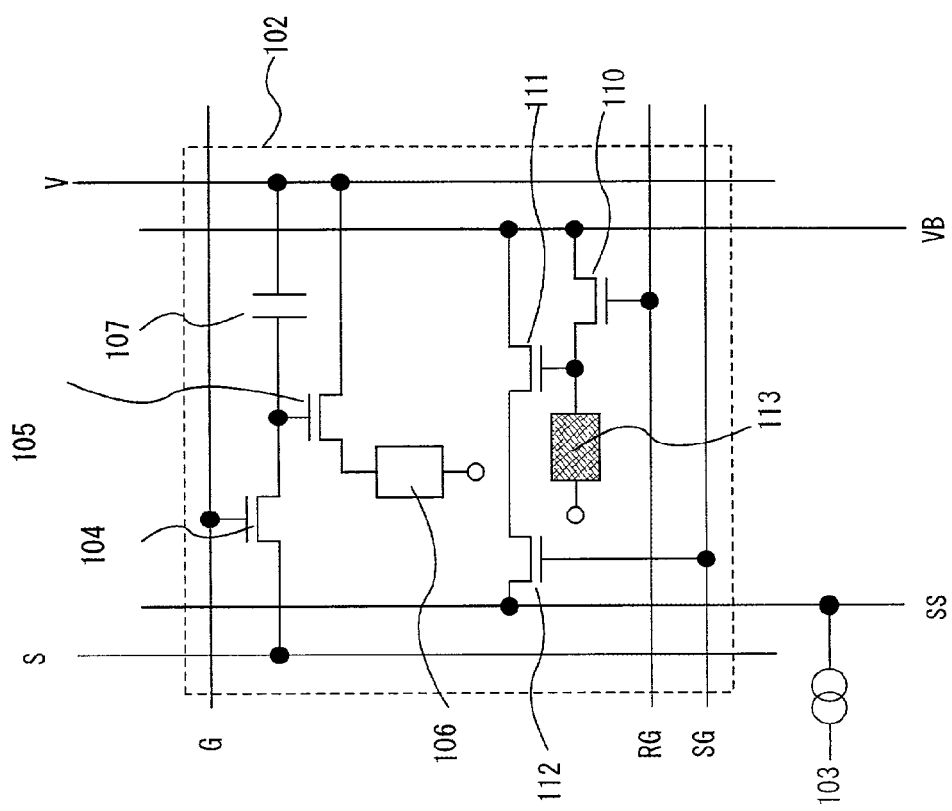
FIG. 8 is a circuit diagram of the pixel.

FIG. 8 shows the detail structure of pixel 102. The area surrounded by the dotted line shows a pixel 102. Furthermore, the source signal line S means either one of source signal lines S1 to Sx. And the power supply line V means either one of power supply lines V1 to Vx. And the gate signal line G means either one of gate signal lines G1 to Gy. And the gate signal line RG for reset means either one of gate signal lines RG1 to RGy for reset. And the gate signal line SG for sensor means either one of gate signal lines SG1 to SGy for sensor. Then the sensor output wire SS means either one of sensor output wires SS1 to SSx.

The pixel 102 has a TFT 104 for switching, a TFT 105 for driving EL and an EL element 106. Further in FIG. 8, while the pixel 102 is provided with a condenser 107, the condenser 107 is not always necessary.

An EL element 106 is composed of an anode, a cathode and an EL layer provided between the anode and the cathode. When the anode is connected with the source region or the drain region of the TFT 105 for driving EL, the anode is the pixel electrode and the cathode is the opposite electrode. On the contrary, if the cathode is connected with the source region or the drain region of the TFT 105 for driving EL, the anode will be the opposite electrode and the cathode will be the pixel electrode.

The gate electrode of the TFT 104 for switching is connected with the gate signal line G. And of the source region and the drain region of the TFT 104 for switching, one is connected with the source signal line S and the other with the gate electrode of the TFT 105 for driving EL.

Of the source region and the drain region of the TFT for driving EL, one is connected with the power supply line V and the other with the EL element 106. The condenser 107 is installed connected with the gate electrode of the TFT 105 for driving EL and the power supply line V.

Furthermore, the pixel 102 has a TFT 101 for reset, a TFT 111 for buffer, a TFT 112 for selection and a photodiode 113.

The gate electrode of the TFT 110 for reset is connected with the gate signal line RG for reset. The source region of the TFT 110 for reset is connected with the power supply line VB for sensor. The power supply line VB for sensor is always maintained to a constant potential (the reference potential). Further the drain region of the TFT 110 for reset is connected with the photodiode 113 and the gate electrode of the TFT 111 for buffer.

It is not illustrated, but the photodiode has a cathode, an anode, and a photoelectric conversion layer provided between the cathode and the anode. The drain region of the TFT 110 for reset is connected in practice with the anode or cathode of photodiode 113.

The drain region of the TFT 111 for buffer is connected with the power supply line VB for sensor and maintained at a constant reference potential. And the source region of the TFT 111 for buffer is connected with the source region or drain region of the TFT 112 for selection.

The gate electrode of the TFT 112 for selection is connected with the gate signal line SG for sensor. And of the source region and the drain region of the TFT 112 for selection, one is connected as above-mentioned to the source region of the TFT 111 for buffer and the other to the sensor output wire SS. The sensor output wire SS is connected with the constant current source 103 (any one of constant current source 103_1 to 103_x) and always a constant current flows in it.

The timing signals from the shift register 120a shown in FIG. 6 are supplied to the latch (A) 120b. The latch (A) 120b has latches at a plurality of stages to process digital signals. The latch (A) 120b writes and holds in order the digital signals at the same time as said timing signals are entered.

Furthermore, when digital signals are taken into the latch (A) 120b, the digital signals can be subsequently input into the latches at a plurality of stages that the latch (A) 120b has. But this invention of application is not limited to this composition. The latches at a plurality of stages that the latch (A) 120b has can be sorted into several groups and the so-called divided driving can be executed by entering digital signals at the same time to each of the groups in parallel. Furthermore, the number of groups in this case is called the division number. For example, when the latches are sorted into groups with 4 stages each, it is driven divided by four divisions.

The time to finish the writing of digital signals to the latches of all stages of latch (A) 120b is called the line period. That is to say, the line period is the time interval, from the time when the writing of digital signal starts at the latch of the most left side stage in the latch (A) 120b, to the time when the writing of digital signals finishes at the latch of the stage the far right side. In practice, the line period can contain the horizontal retrace line period in addition to said line period.

When the line period is finished, a Latch Signal is supplied to the latch (B) 120c. At this moment, the digital signals written and held in the latch (A) 120b are transmitted at once to the latch (B) 120c all together, and written and held in the latches of all stages of the latch (B) 120c.

The latch (A) 120b which has finished to transmit digital signals to the latch (B) 120c executes again the writing of digital signals in order according to the timing signals from the shift register 120a.

During this 1 line period of the second cycle, the digital signals, which are written and held in the latch (B) 120b, are entered to the source signal lines S1-Sx.

On the other hand, each of the drive circuits 122 of the gate signal side has a shift register and a buffer (non of these are illustrated). But as the case may be, the drive circuits 122 of the gate signal side can have a level shift in addition to the shift register and buffer.

At the drive circuits 122 on gate signal side, gate signals from the shift register (not shown) are supplied to the buffer (not shown), then to the corresponding gate signal line. To each of the gate signal lines G1 to Gy, a gate electrode of TFT 104 for switching pixels for 1 line is connected and, as all the TFT 104 for switching the pixels for 1 line should be on at the same time, a buffer which permits a big current flow is used.

Furthermore, the number, composition and actions of the source signal line drive circuits and of the gate signal line drive circuits are not limited to the composition of this embodiment. The area sensor used in the sensor-incorporated display of the invention is able to use well-known source signal line drive circuits and gate signal line drive circuits.

The composition of this embodiment can be executed in any combination with the embodiment 1.

[Embodiment 3]

Figure 9:
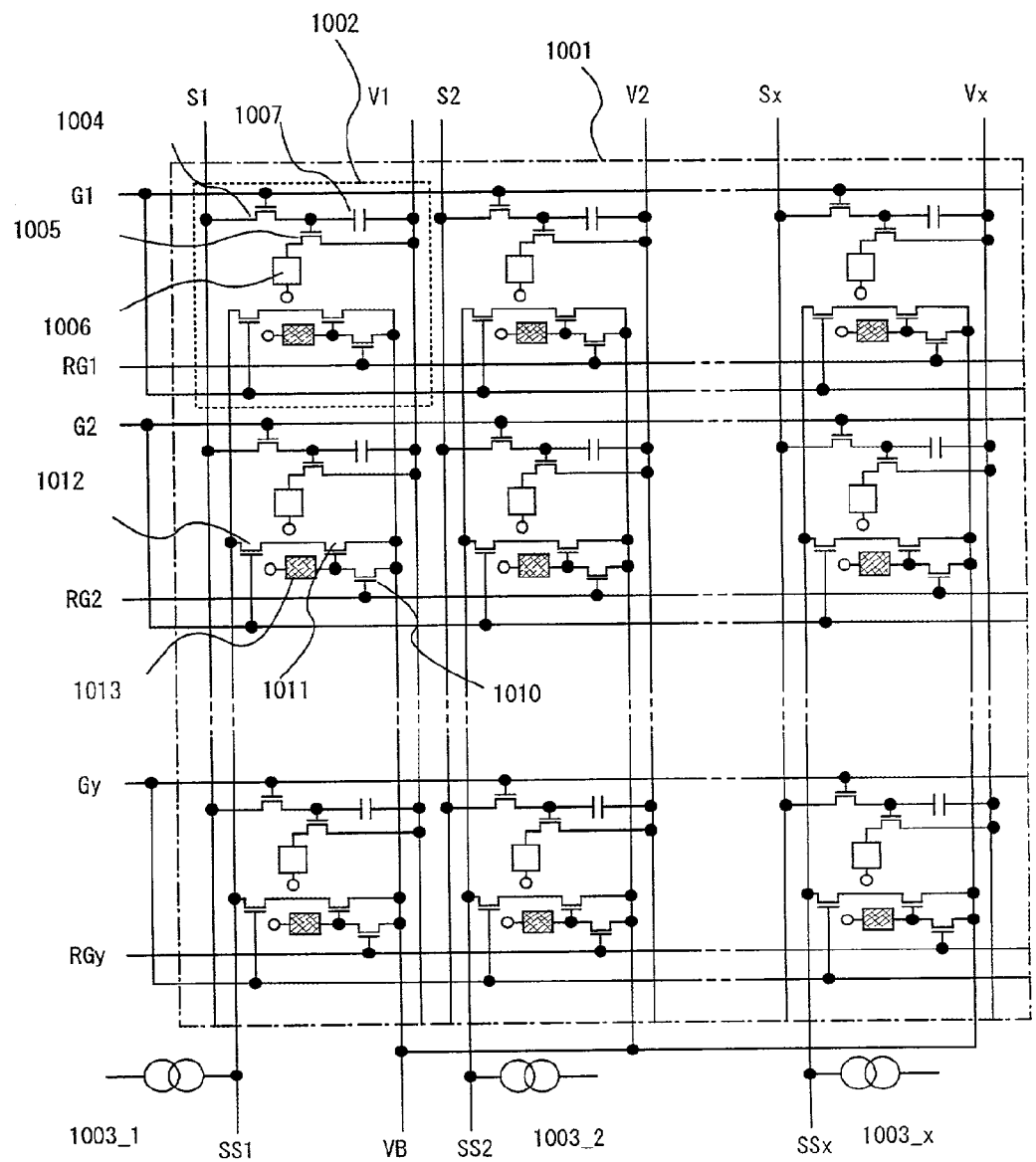
FIG. 9 is a circuit diagram of the sensor portion.

A circuit diagram of the sensor portion with different composition from the sensor portion of the embodiment 2 is shown in FIG. 9. The sensor portion 1001 is provided with the source signal lines S1 to Sx, power supply lines V1 to Vx, gate signal lines G1 to Gy, gate signal lines RG1 to RGy for reset, sensor output wires SS1 to SSx and power supply line VB for sensor.

The sensor portion 1001 has a plurality of pixels 1002. The pixel 1002 has either one of source signal lines S1 to Sx, either one of power supply lines V1 to Vx, either one of gate signal lines G1 to Gy, either one of gate signal lines RG1 to RGy for reset, either one of sensor output wires SS1 to SSx and the power supply line VB for sensor.

Each of the sensor output wires SS1 to SSx is connected with the constant current source 1003_1 to 1003_x respectively.

The pixel 1002 has a TFT 1004 for switching, a TFT 1005 for driving EL and an EL element 1006. Further in FIG. 9 the pixel 1002 is provided with a condenser 1007, but the condenser 1007 is not always required. Furthermore, the pixel 1002 has a TFT 1010 for reset, a TFT 1011 for buffer, a TFT 1012 for selection and a photodiode 1013.

The EL element 1006 is composed of an anode, a cathode, and an EL layer provided between the anode and the cathode. When the anode is connected with the source region or drain region of the TFT 1005 for driving EL, the anode is the pixel electrode and the cathode is the opposite electrode. On the contrary, if the cathode is connected with the source region or drain region of the TFT 1005 for driving EL, the anode will be the opposite electrode and the cathode the pixel electrode.

The TFT 1004 for switching is connected with the gate signal lines (G1 to Gy). And of the source region and the drain region of the TFT 1004 for switching, one is connected with the source signal line S and the other with the gate electrode of the TFT 1005 for driving EL.

Of the source region and the drain region of the TFT 1005 for driving EL, one is connected with the power supply lines (V1 to Vx) and the other is connected with the EL element 1006. The condenser 1007 is connected with the gate electrode of TFT 1005 for driving EL and with the power supply lines (V1 to Vx).

The gate electrode of the TFT 1010 for reset is connected with the gate signal lines (RG1 to RGx) for reset. The source region of TFT 1010 for reset is connected with the power supply line VB for sensor. The power supply line VB for sensor is always maintained at a constant potential (the reference potential). Further the drain region of TFT 1010 for reset is connected with the photodiode 1013 and with the gate electrode of TFT 1011 for buffer.

Though it is not illustrated in the figure, the photodiode 1013 has a cathode, an anode, and a photoelectric conversion layer provided between the cathode and the anode. The drain region of TFT 1010 for reset is connected in practice with the cathode or anode of photodiode 1013.

The drain region of TFT 1011 for buffer is connected with the power supply line VB for sensor and maintained always at the constant reference potential. And the source region of TFT 1011 for buffer is connected with the source region or drain region of TFT 1012 for selection.

The gate electrode of TFT 1012 for selection is connected with the gate signal lines (G1 to Gx). And of the source region and the drain region of TFT 1012 for selection, one is connected as above-mentioned to the source region of TFT 1011 for buffer and the other is connected to the sensor output wires (SS1 to SSx). Each of the sensor output wires (SS1 to SSx) is connected with the constant current source 1003 (constant current source 1003_1 to 1003_x) and always a constant current flows.

In this embodiment, the TFT 1004 for switching and the TFT 1012 for selection have identical polarity. That is to say, when the TFT 1004 for switching is a TFT of n-channel type, the TFT 1012 for selection is a TFT of n-channel type also. And if the TFT 1004 for switching is a TFT of p-channel type, the TFT 1012 for selection is a TFT of p-channel type also.

Furthermore, the sensor portion of area sensor of this embodiment is different from the area sensor illustrated in FIG. 7, but the gate electrode of TFT 1004 for switching and the gate electrode of TFT 1012 for selection are both connected with the gate signal lines (G1 to Gx). Consequently, in case of the area sensor of this embodiment, the light emission period of EL element 1006 contained in each pixel is the same length as the sampling period (ST1 to STn). By the composition above-mentioned, the area sensor of this embodiment can have less number of lines compared with that of FIG. 7.

Furthermore, the area sensor of this embodiment, is also able to display an image on its sensor portion 1001.

The composition of this embodiment can be effectuated with any combination with the embodiment 1 or the embodiment 2.

[Embodiment 4]

Figure 10:
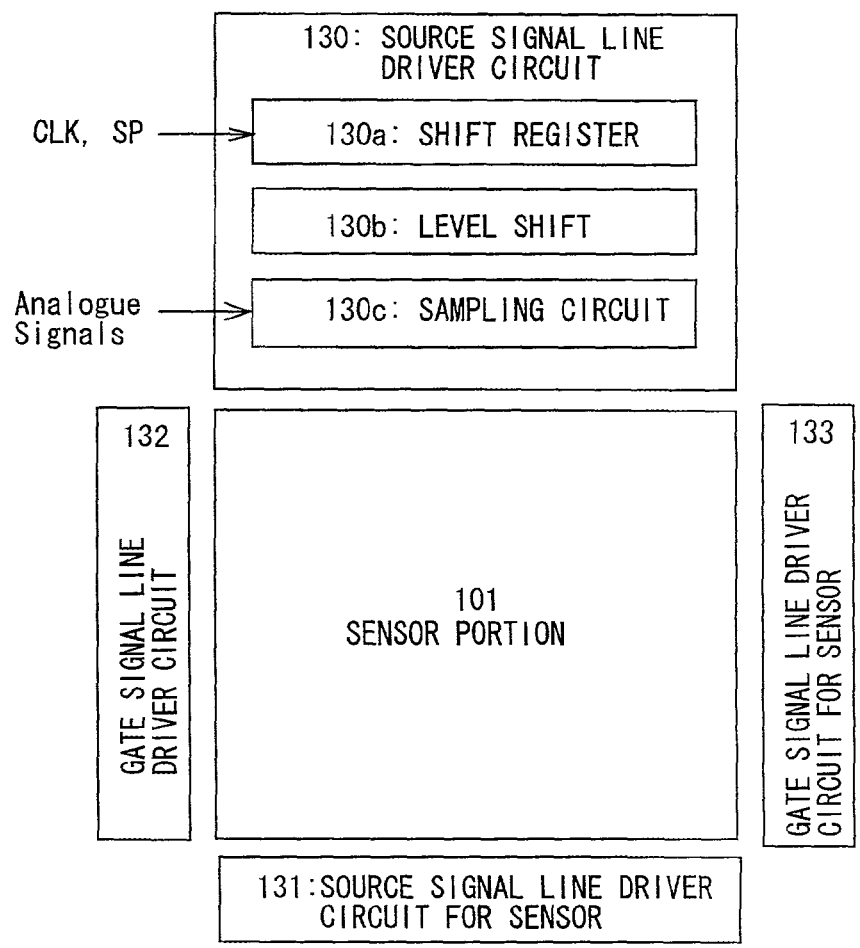
FIG. 10 is a block diagram showing the structure of the sensor-incorporated display.

The top view of the area sensor of this embodiment is shown in FIG. 10. 130 denotes the source signal line drive circuit and 132 denotes the gate signal line drive circuit. Then, 131 denotes the source signal line drive circuit for sensor and 133 denotes the gate signal line drive circuit for sensor. In this embodiment, each one of the source signal line drive circuits and the gate signal line drive circuits are provided, but this invention for application is not limited to this composition. Two source signal line drive circuits can be provided. Furthermore, Two gate signal line drive circuits can be also provided.

Further in this description, the source signal line drive circuit 130, gate signal line drive circuit 132, source signal line drive circuit 131 for sensor, and gate signal line drive circuit 133 for sensor are called the driving part.

The source signal line drive circuit 130 has a shift register 130a, a level shift 130b and a sampling circuit 130c. Furthermore, the level shift is used only when it is needed and is not always required. Furthermore, in this embodiment the level shift is installed between the shift register 130a and the sampling circuit 130c, but this invention for application is not limited to this composition. So, it can be of the composition where the level shift 130b is installed in the shift register 130a.

The clock signal (CLK) and the start pulse signal (SP) are entered into the shift register 130a. From shift register 130a, the sampling signal is output in order to sample the analogue signal (analog signal). The output sampling signal is entered into the level shift 130b and then output with it's potential of bigger amplitude.

The sampling signal sent from the level shift 130b is entered into the sampling circuit 130c. Then the analog signals entering into the sampling circuit 130c are sampled respectively by sampling signals and entered into the source signal lines S1 to Sx.

On the other hand, the drive circuits 132 on the gate signal side have each a shift register and a buffer (none of them are illustrated). Depending on the case, the drive circuit 132 on the gate signal side can have a level shift in addition to the shift register and the buffer.

At the drive circuits 132 on gate signal side, the gate signals from the shift register (not illustrated) is supplied to the buffer (not illustrated), then to the corresponding gate signal line. To each of the gate signal lines G1 to Gy a gate electrode of TFT 104 for switching pixels for 1 line is connected, and as all the TFT 104 for switching the pixels for 1 line should be ON at the same time, a buffer which permits a big current flow is used.

Furthermore, the number, composition and actions of the source signal line drive circuits and of the gate signal line drive circuits are not limited to the composition of this embodiment. The area sensor used in the sensor-incorporated display of the invention permits the use of well-known source signal line drive circuits and gate signal line drive circuits.

Further in this embodiment, the sensor portion 101 can be of the composition shown in FIG. 7 or FIG. 9.

This embodiment can be used in any combination with the embodiment 1 or the embodiment 3.

[Embodiment 5]

In this embodiment, a production method of the TFT of the sensor portion on the substrate will be described in details.

At first, as shown in FIG. 11A, on the substrate 700 composed of the glass, such as barium boro-silicated glass, typically #7059 glass or #1737 glass of Coning Co. Ltd. or aluminum boro-silicated glass, is formed a primary film 701 composed of an insulating film, such as silicon oxide film, silicon nitride film or silicon oxide nitride film. For example, a silicon oxide nitride film 701a fabricated from SiH$_4$, NH$_3$ and N$_2$O by plasma CVD method is formed for 10 to 200 nm (preferably 50 to 100 nm), and a silicon oxide nitride hydride film 701b fabricated in the same way from SiH$_4$ and N$_2$O is formed by laminating in a thickness of 50 to 200 nm (preferably 100 to 150 nm). In this embodiment the primary film 701 is shown in a double layer structure, but it can be formed in a structure with a single layer film or multiple layers of the above-mentioned insulating films.

The semiconductor islands 702 to 707 are formed with crystalline semiconductor films of which semiconductor film having an amorphous structure is fabricated by the laser crystallization method or a well-known thermal crystallization method. The thickness of the semiconductor islands 702 to 707 is formed at 25 to 80 nm (preferably 30 to 60 nm). There is no restriction on the material used for the crystalline semiconductor films, but they are preferably formed with silicon or silicon-germanium (SiGe) alloy.

When the crystalline semiconductor film is fabricated by the laser crystallization method, the excimer laser, YAG laser or YVO$_4$ laser of pulse oscillation type or continuous emission type. When these lasers are used, it is preferable to use a method consisting of condensing in linear form the laser light radiated from the laser oscillator and irradiating them on the semiconductor film by optical system. The condition of crystallization is normally chosen as appropriate by the person who performs, but when the excimer laser is used, the pulse oscillatory frequency should be of 30 Hz and the laser energy density of 100 to 400 mJ/cm$^2$ (typically of 200 to 300 mJ/cm$^2$). If YAG laser is used, the second higher harmonics should be used with the pulse oscillatory frequency of 1 to 10 kHz, and preferably with the laser energy density of 300 to 600 mJ/cm$^2$ (typically of 350 to 500 mJ/cm$^2$). Then the laser light condensed in linear form of a width of 100 to 1000 μm, for example, of 400 μm is irradiated over the total surface of the substrate, with an overlap rate at this time of the linear laser light of 80 to 98%.

Then, a gate insulating film 708 covering the semiconductor islands 702 to 707 is formed. The gate insulating film 708 is fondled by the plasma CVD method or sputtering method in a film of a thickness of 40 to 150 nm containing silicon. In this embodiment, it is formed in a silicon oxide nitride film of a thickness of 120 nm. Of course, the gate insulating film 708 is not limited to the silicon oxide nitride film as such, but other silicon-containing insulating film can be used in a single layer or multi-layer structure. For example, when a silicon oxide film is used, it can be formed by mixing TEOS (Tetraethyl Orthosilicate) and O$_2$ by the plasma CVD method and electrically discharged with the reaction pressure of 40 Pa, at a substrate temperature of 300 to 400° C., and with a high frequency (13.56 MHz) electric power density of 0.5 to 0.8 W/cm$^2$. With a silicon oxide film fabricated like this, good characteristics as a gate insulating film can be obtained by a subsequent thermal anneal at 400 to 500° C.

Then, the first conductive film 709a and second conductive film 709b are formed to form a gate electrode on the gate insulating film 708. In this embodiment, the first conductive film 709a is formed with Ta in a thickness of 50 to 100 nm and the second conductive film 709b with W in a thickness of 100 to 300 nm.

The Ta film is formed by the sputtering method, sputtering the target of Ta by Ar. In this case, if an appropriate quantity of Xe or Kr is added to Ar, the inner stress of Ta film is relieved to prevent the film from peeling. Furthermore, the resistibility of the Ta film of α phase is approximately 20 μW and usable for an gate electrode, but the resistibility of the Ta film of β phase is approximately 180 μW cm and not suitable for a gate electrode. In order to form a Ta film of α phase, it can be easily formed if tantalum nitride, which has a crystal structure close to α phase of Ta, is in advance formed as a base for Ta in a thickness of approximately 10 to 50 nm.

When W film is formed, it is formed by the sputtering method with W as target. Otherwise, it can be formed also by a thermal CVD method using tungsten hexafluoride (WF$_6$). In any way, it is necessary to lower the resistibility to be used as a gate electrode, preferably to less than 20 μW cm for the resistibility of W film. The resistibility of W film can be lowered by having greater crystal grains, but if there are many impure elements like oxygen in the W, the crystallization could be prevented to increase the resistibility. For this reason, when the sputtering method is used, a W target of purity 99.9999% is used and sufficient precaution is taken to avoid the mixture of impurities from the gaseous phase during the film formation in order that a resistibility of 9 to 20 μW cm can be realized.

Furthermore, in this embodiment the first conductive film 709a is made with Ta and the second conductive film 709b with W, but they are not restrictive, either of them being able to be formed with an element chosen from Ta, W, Ti, Mo, Al and Cu, or with an alloy material or compound material of which the main component is one of said elements. Furthermore, one can use a semiconductor film typically represented by polycrystal silicon film after doping the impure elements such as phosphorus. The examples of preferable combinations, other than this embodiment, are forming the first conductive film 709a with tantalum nitride (TaN) and the second conductive film 709b with W, forming the first conductive film 709a with tantalum nitride (TaN) and the second conductive film 709b with Al, and forming the first conductive film 709a with tantalum nitride (TaN) and the second conductive film 709b with Cu.

Then, the masks 710 to 715 are formed by a resist and an etching treatment is carried out in order to form the electrodes and the wires. In this embodiment, ICP (Inductively Coupled Plasma) etching method is used, in which CF$_4$ and Cl$_2$ are mixed to the etching gas and RF (13.56 MHz) electric power of 500 W is supplied to the coil type electrode at a pressure of 1 Pa to generate plasma. To the substrate side (sample stage) also, the RF (13.56 MHz) electric power of 100 W is supplied to apply significantly a negative self-bias voltage. If CF$_4$ and Cl$_2$ are mixed, W film and Ta film are both etched to almost the same extent.

Under the above-mentioned condition of etching, by making the form of the masks appropriate by means of the resist and by the effect of the bias voltage applied to the substrate side, the edge shape of the first conductive layer and second conductive layer become tapered. The angles of the tapered parts are 15 to 45°. In order to etch without leaving residuals on the gate insulating film, it is preferable to increase etching time by around 10 to 20%. Because the selectivity of the silicon oxide nitride film against the W film is 2 to 4 (typically 3), the surfaces where silicon oxide nitride film is exposed will be etched to around 20 to 50 nm by an over-etching treatment. In this way, by means of the first etching treatment, the conductive layers 719 to 724 of the first shape composed of the first conductive layer and the second conductive layer are formed (the first layers 719a to 724a and the second layers 719b to 724b). 718 denotes an insulating film, and the region which is not covered by the first shaped conductive layers 719 to 724 is etched up to around 20 to 50 nm to form a thin region. (FIG. 11B)

Then, the first doping treatment is carried out and an impure element is added to give an n-type. (FIG. 11C) The doping can be carried out by an ion doping method or ion implantation method. The ion doping method is carried out under condition of the dose of $1\times10^{13}$ to $5\times10^{14}$ atoms/cm$^2$, with the accelerating voltage of 60 to 100 keV. For the impure element, which gives n-type, the elements of 15 group, typically the phosphorus (P) or the arsenic (As), are used, and the phosphorus (P) is used here. In this case, The conductive layers 719 to 724 become a mask against the impure element which gives n-type and impurity regions 726 to 731 are formed in a self-matching way. To the first impurity regions 726 to 731, the impure element is added at the concentration between $1\times10^{20}$ to $1\times10^{21}$ atoms/cm$^3$ to give n-type.

Then, the second etching treatment is carried out as shown in FIG. 11D. Likewise, the ICP etching method is used, in which CF$_4$, Cl$_2$ and O$_2$ are mixed to the etching gas and RF electric power (13.56 MHz) of 500 W is supplied to the coil type electrode at a pressure of 1 Pa to generate plasma. To the substrate side (sample stage), RF (13.56 KHz) electric power of 50 W is input to apply a self-bias voltage lower than the first etching treatment. By these conditions the W film is etched anisotropically and then the first conductive layer Ta is etched anisotropically in a lower etching speed in order to form the second shaped conductive layers 733 to 738 (the first conductive layers 733a to 738a and the second conductive layers 733b to 738b). 732 denotes a gate insulating film, the region which is not covered by the second shaped conductive layers 733 to 738 is etched further up to around 20 to 50 nm and forms a thin region.

The etching reaction of the W film and the Ta film by the mixed gas of CF$_4$ and Cl$_2$ can be supposed by the radicals or ionic species generated and the vapor pressure of reaction products. When the vapor pressures of fluoride and chloride of W and Ta are compared, WF$_6$ which is a fluoride of W is extremely important and other WCl$_5$, TaF$_5$ and TaCl$_5$ are almost the same. Accordingly, both the W film and Ta film are etched by the mixed gas of CF$_4$ and Cl$_2$. However, if an appropriate quantity of O$_2$ is added to this mixed gas, CF$_4$ and O$_2$ react to become CO and F, and a large quantity of F radical and F ion are generated. As a result of this, the etching speed of W film with higher vapor pressure of fluoride increases. On the other hand, for Ta there is relatively less increase of etching speed by the increase of F. Furthermore, as Ta is easily oxidized, the surface of Ta is oxidized by the addition of O$_2$. As the oxides of Ta do not react with the fluorine or the chlorine, the etching speed of Ta film decreases further. In consequence, it becomes possible to differentiate the etching speed of W film and Ta film in order to have the etching speed of W film greater than that of Ta film.

Figure 12A:
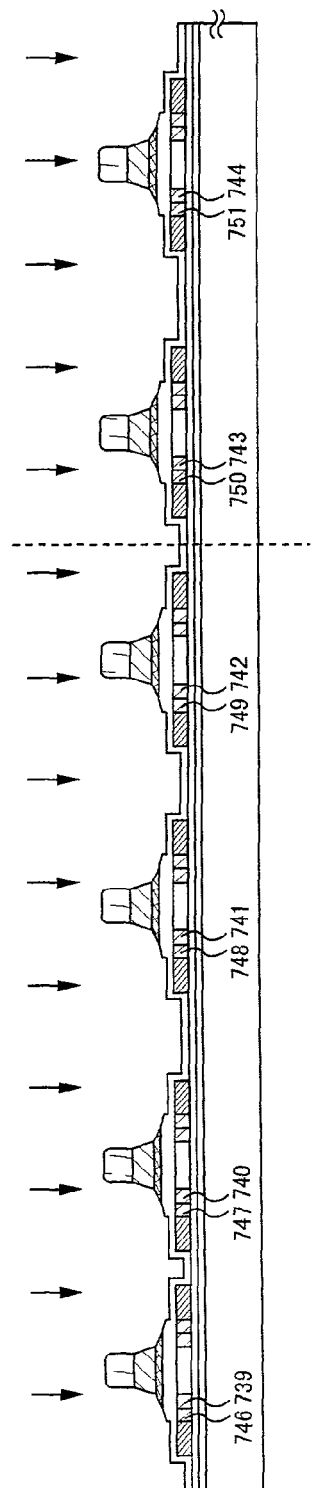
FIGS. 12A to 12C are drawings showing the fabrication process of the sensor-incorporated display.

Then, the second doping treatment is executed as shown in FIG. 12A. In this case, with the conditions of less dose and higher accelerating voltage than the first doping treatment, the impure element giving the n-type is doped. For example, executing with the accelerating voltage of 70 to 120 keV and the dose of $1\times10^{13}$/cm$^2$, new impurity region is formed in the interior of the first impurity region formed on the semiconductor islands as shown in FIG. 11C. The doping will be effectuate, by using as masks the second shaped conductive layers 733 to 738, so as to the impure element to be added also to the region under the second conductive layers 733a to 738a. Of this way, the third impurity regions 739 to 744, which overlap the second conductive layers 733a to 738a, and the second impurity regions 746 to 751 between the first impurity regions and the third impurity regions. The impure element which gives the n-type will be determined for the concentration to be $1\times10^{17}$ to $1\times10^{19}$ atoms/cm$^3$ in the second impurity regions and $1\times10^{16}$ to $1\times10^{18}$ atoms/cm$^3$ in the third impurity regions.

Figure 12B:
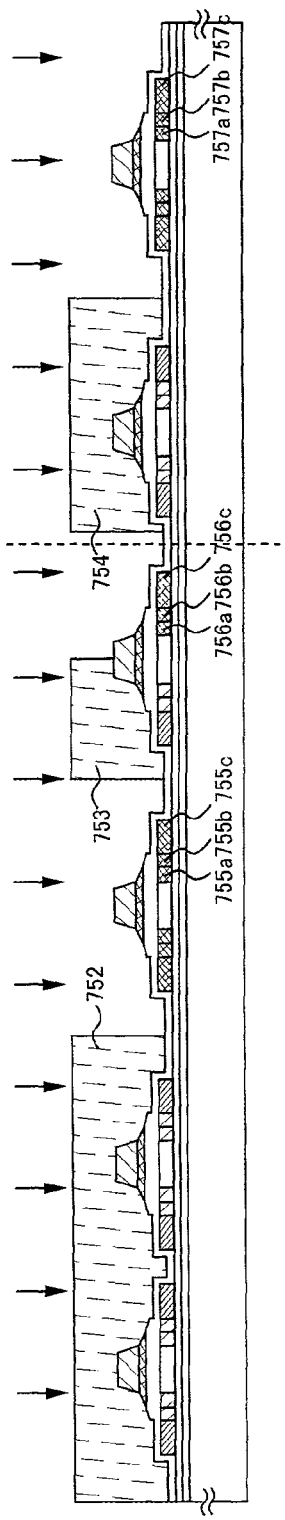

Then, as shown in FIG. 12B, at the semiconductor islands 704 and 707 which form TFT of p-channel type, the fourth impurity regions 755 to 757 are formed with the conductive type contrary to the negative conductive type. By using as masks against the impure elements, the second conductive layers 735b and 738b, the impurity regions are formed in a self-matching manner. At this moment, all the surface of the semiconductor islands 702, 703 and 706 and a part of 705, which form TFT of n-channel type, should be in advance covered by the resist masks 752 to 754. Although the impurity regions 755a to 755c, 756a to 756c, and 757a to 757c are added of phosphorus with different concentrations, they are formed by the ion doping method using the diborane (B$_2$H$_6$), the impurity concentration of all the regions being $2\times10^{20}$ to $2\times10^{21}$ atoms/cm$^3$.

By the above-mentioned processes the impurity region is formed in each to semiconductor island. The second conductive layers 733 to 738, which overlaps the semiconductor islands, work as the electrodes.

Figure 12C:
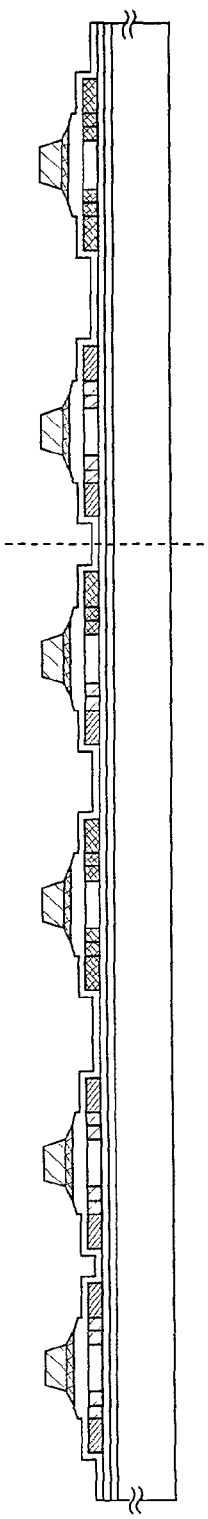

After having eliminated the resist masks 752 to 754, a process of activation of the impure element added to each semiconductor island should be executed for the aim of controlling the conductive type as shown in FIG. 12C. This step is carried out by a thermal annealing method by means of an annealing furnace. Otherwise, a laser annealing method or a rapid thermal annealing (RTA) method can be applied. The thermal annealing method is normally carried out in the nitrogen atmosphere of oxygen concentration of less than 1 ppm, preferably of less than 0.1 ppm and at a temperature of 400 to 700° C., typically at 500 to 600° C., and in this embodiment it is carried out at 500° C. during 4 hours. However, If the wiring material utilized for 733 to 738 is weak to the heat, it is preferred to execute the activation after having formed interlayer insulating film (with silicon as the main component) in order to protect the wires, etc.

Furthermore, in the atmosphere containing 3 to 100% of hydrogen, a heat treatment is carried out at 300 to 450° C. during 1 to 12 hours as a step of hydrogenation of the semiconductor islands. This step is a step to terminate the dangling bond of semiconductor layers by means of the thermally excited hydrogen. As an another means of hydrogenation, the plasma hydrogenation (which uses the hydrogen excited by plasma) can be carried out.

Next, the first interlayer insulating film 760 is formed in a thickness of 100 to 200 nm from the silicon oxide nitride film. On this film, the second interlayer insulating film 761 is formed consisting of organic insulating material. Then, an etching step is executed in order to form contact holes.

Figure 13A:
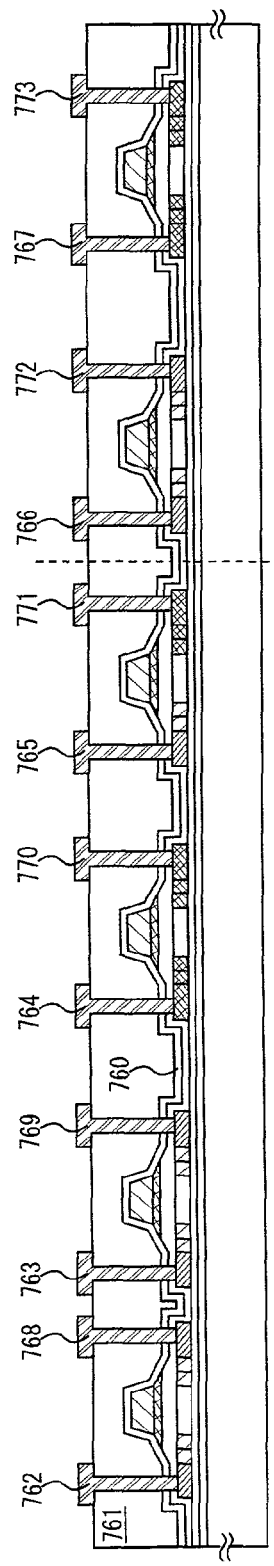
FIGS. 13A to 13C are drawings showing the fabrication process of the sensor-incorporated display.

Then, the source wires 762 to 767, which form a contact with the source region to of semiconductor islands, the drain wires 768 to 773, which form a contact with the drain region, are formed. Not shown in the figure, in this embodiment this electrode is used as an electrode of 3-layer structure formed continuously by a sputtering method a Ti film of 100 nm, an Al film containing Ti of 300 nm and a Ti film of 150 nm (FIG. 13A).

Then, the passivation film 774 is formed so as to cover the source wires 762 to 767, the drain wires 768 to 773 and the second interlayer insulating film 761. The passivation film 774 is formed of a silicon nitride film at a thickness of 50 nm. Furthermore, the third interlayer insulating film 775 consisting of an organic resin is formed in thickness around of 1000 nm. For the organic resin film, polyimide, acrylic, polyimideamide, etc. can be used. The advantages of using an organic resin film, that the formation of it is easy, the parasitic capacitance can be decreased because the relative permittivity is low, and the excellent planarization, etc. can be mentioned.

Furthermore, other organic resin film than those mentioned above also can be used. Here, after applied to the substrate, a type of polyimide, which thermally polymerize, is used to form it by burning at 300° C.

Figure 13B:
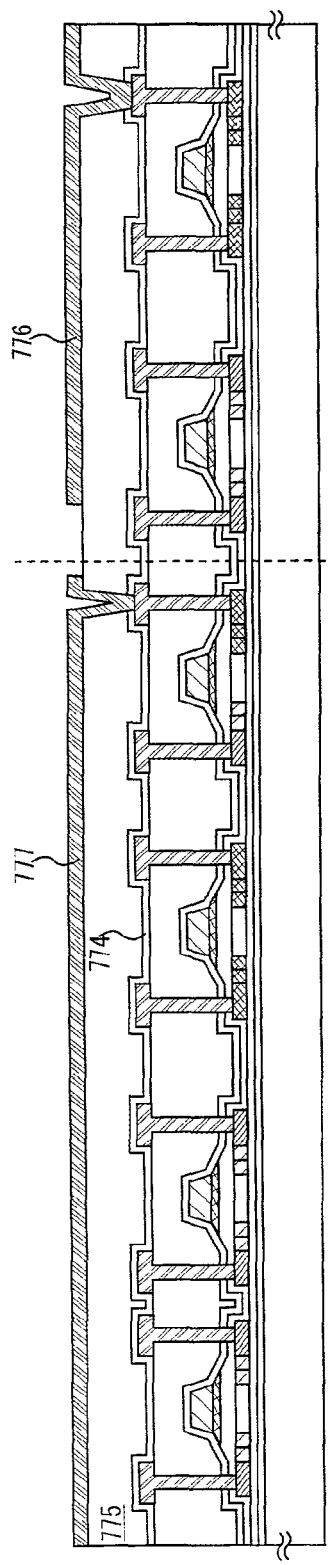

Then, the contact holes are formed to reach the drain wires 773 and 771 on the third interlayer insulating film 775 and the passivation film 774, and the pixel electrode 776 and the wire for sensor 777 are formed. In this embodiment, a indium-tin oxide (ITO) film is formed at a thickness of 110 m, and the wire for sensor 777 and the pixel electrode 776 are formed at the same time by patterning. Furthermore, a transparent conductive film by mixing 2 to 20% of zinc oxide to the indium oxide can also be used. This pixel electrode 776 will be the anode of EL element (FIG. 13B).

Then, the bank 778 is formed of a resin material. The bank 778 can be formed by patterning of acrylic film or polyimide film of a thickness 1 to 2 μm. This bank 778 is formed between the pixels in a form of stripe. In this embodiment, the bank 778 is formed along on the source wire 776 but it can be also formed along on the gate wire (not illustrated). Furthermore, the material forming the bank 778 can be mixed with a pigment or the like to use it as a shield film.

Also, at the same time as the bank 778 is formed, on the contact hole of pixel is electrode 776 reaching to the drain wire 773, a planarization part can be formed to make plane the EL layer which is formed on the pixel electrode 776.

Then, the EL layer 779 and cathode (MgAg electrode) 780 are formed successively by the vacuum evaporation method without atmospheric release. Furthermore, the film thickness of EL layer 779 can be of 80 to 200 nm (typically of 100 to 120 nm) and the thickness of cathode 780 can be of 180 to 300 nm (typically of 200 to 250 nm). Furthermore, while only one pixel is illustrated in this embodiment, the EL layer emitting red color, the EL layer emitting green color and the EL layer emitting blue color are also formed simultaneously.

In this process, the EL layers 779 and the cathodes 780 are formed successively for the pixel corresponding to red color, the pixel corresponding to green color and the pixel corresponding to blue color. However, as the EL layer 779 is not so resistant to solution, each color must be formed separately without using the photolitography technology. This is preferably carried out by hiding all other pixels except the desired one by means of a metal mask in order to form selectively the EL layer 779 and the cathode 780 only for the required part.

That is to say, firstly a mask is set to hide all the pixels except the pixel corresponding to red color and selectively the red color emitting EL layer and cathode are formed by means of this mask. Then a mask is set to hide all the pixels except the pixel corresponding to green color and selectively the green color emitting EL layer and cathode are formed by means of this mask. Then in the same manner, a mask is set to hide all the pixels except the pixel corresponding to blue color and selectively the blue color emitting EL layer and cathode are formed by means of this mask. Furthermore, in this example it is explained to use different masks for different colors, but only one mask can be used for different colors. Furthermore, it is preferable to continue the treatment to form the EL layer and cathode for all pixels without disrupting the vacuum.

Furthermore, while in this embodiment the EL layer 779 has a single layer structure consisting only of a light emission layer, but the EL layer may have also a hole transport layer, a hole injection layer, an electron transport layer, an electron injection layer, etc. In this way, there have already been reported various combinations and any of these can be used. For EL layer 779 well known materials can be used. As the well-known materials, an organic material is suitable in taking account of the EL-drive voltage. Furthermore, while in this embodiment a MgAg electrode is used for the cathode of EL element, but other well-known materials can be used as well.

Figure 13C:
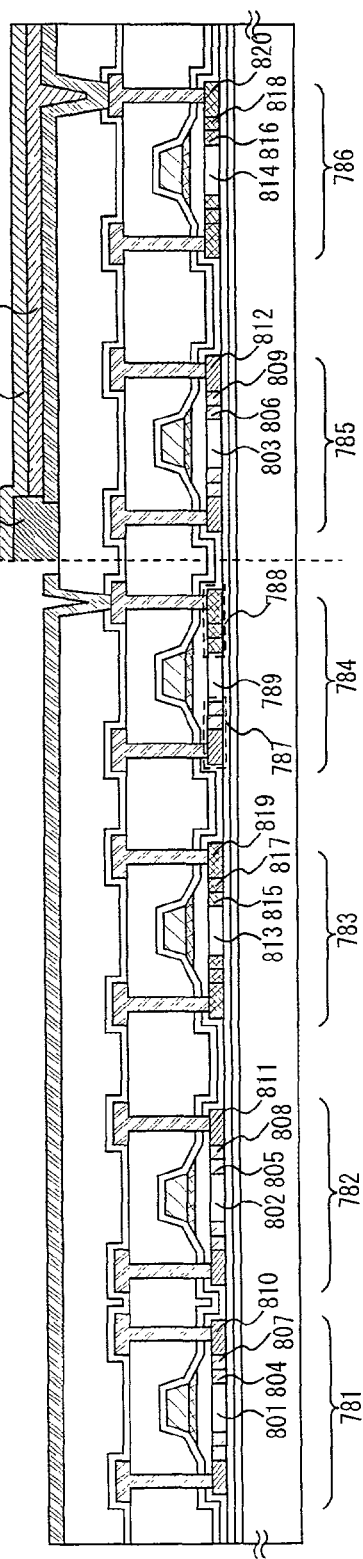

In this way, a sensor substrate of the structure shown in FIG. 13C can be achieved. Furthermore, it is effective to continuously execute processes of forming the bank 778 and cathode 780 by using a thin film forming device of the multi-chamber system (or in-line system) without atmospheric release.

Furthermore, in this embodiment, the processes of fabrication of TFTs contained in the sensor portions are explained, but the TFTs contained in the driving parts also can be formed on the substrate at the same time with reference to the above-mentioned process.

781 denotes the TFT for buffer, 782 denotes the TFT for selection, 783 denotes to the TFT for reset, 784 denotes the photodiode, 785 denotes the TFT for switching and 786 denotes the TFT for driving.

Though in this embodiment the TFT 785 for switching is made in a single gate structure, it can be a double gate structure, triple gate structure, or a multi-gate structure having more than three gates. By making the TFT 785 for switching have the double gate structure, it becomes a structure having in practice two TFTs connected in series and has an advantage to permit to reduce the off-current.

Then in this embodiment, the gate electrode 736, which is installed on the photodiode 784, is maintained at a potential at which there is no current flow through the photoelectric conversion layer 789 which is provided between the cathode 787 and the anode 788.

In this embodiment, TFT 781 for buffer, TFT 782 for selection, TFT 785 for switching are the TFT of n-channel type, and each one of them has the channel forming regions 801 to 803, the third impurity regions 804 to 806 (Lov region) overlapping the first gate electrodes 733a, 734a and 737a, the second impurity regions 807 to 809 (Loff region) formed on the outside of the first gate electrodes 733a, 734a and 737a, and the first impurity regions 810 to 812 functioning as source region or drain region.

Further in this embodiment, TFT 783 for reset and TFT 786 for driving EL are the TFT of p-channel, and each TFT has the channel forming regions 813 and 184, the fourth impurity regions 815 and 816 overlapping the first gate electrodes 735a and 738a, the fifth impurity regions 817 and 818 formed on the outside of the first gate electrodes 735a and 738a, and the sixth impurity regions 819 and 820 functioning as source region or drain region.

In fact, when achieved up to FIG. 13C, it is preferable to protect them from the open air by means of a packaging (encapsulation) with a highly air tight and less degassing protective film (laminate film, ultraviolet curing resin film, etc.) or a transparent sealing material. At this time, one can increase the reliability of EL elements by making the inside of the sealing material filled with inert atmosphere or by arranging a hygroscopic substance (for example, barium oxide) in the inside.

Furthermore, when the air tightness becomes higher by a process, for example, of packaging, connectors (flexible print circuit: FPC) to connect the terminals, which are drawn from the elements and circuits formed on the substrate, with the external signal terminals installed to achieve it as a final product. In this specification, a product ready for delivery like this shall be called an area sensor.

Furthermore, this invention is not limited to the above-mentioned method of fabrication and it is possible to fabricate by a well-known method. Furthermore, this embodiment can be effectuated in any combination with embodiments 1 through 4.

[Embodiment 6]

This embodiment is to describe the situations in which this invention is used. If the identification of an individual does not require such a high degree of identification such as a biological information, it is possible to not use this invention. In the case of transferring a small amount of money, for example, this is not necessarily required.

For this reason, there is a possibility to choose whether the identification is necessary or not and to set up to make the identification selectively, for example, only for the cases where the transfer of a large amount of money is involved. It is also possible to use it according to the situations of clients, or to set up in advance the criteria for judgement on the control microcomputer of portable communication device and use it only in the cases where the numeric value is more than a certain value. Furthermore, it is possible to transmit through the Internet the identification result only when the identification result is required.

Furthermore, this embodiment can be effectuated in any combination with embodiments 1 through 5.

[Embodiment 7]

This embodiment describes an example of fabrication of EL (electro-luminescence) display (area sensor) which is used for the sensor-incorporated display of this invention. Furthermore, FIG. 14A is a top view of the EL display of this invention and FIG. 14B is the sectional view.

Figure 14A:
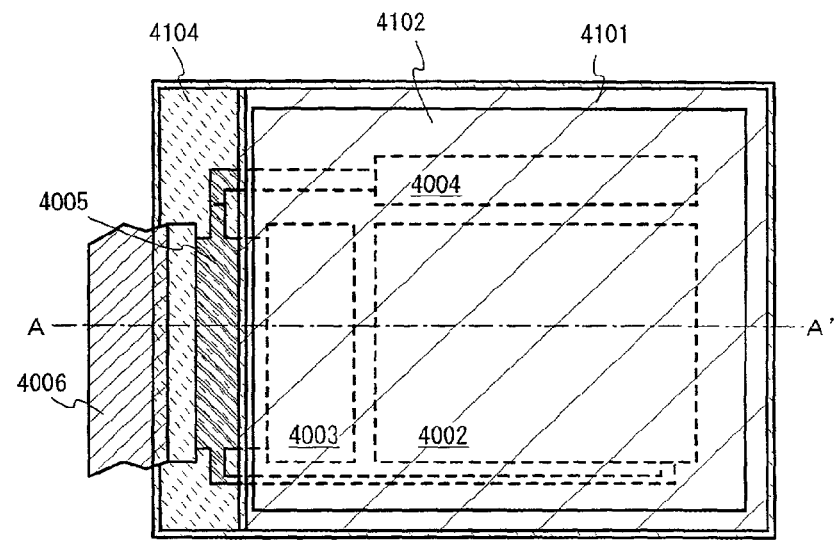
FIGS. 14A and 14B are an external view and a sectional view of the sensor-incorporated display, respectively.
Figure 14B:
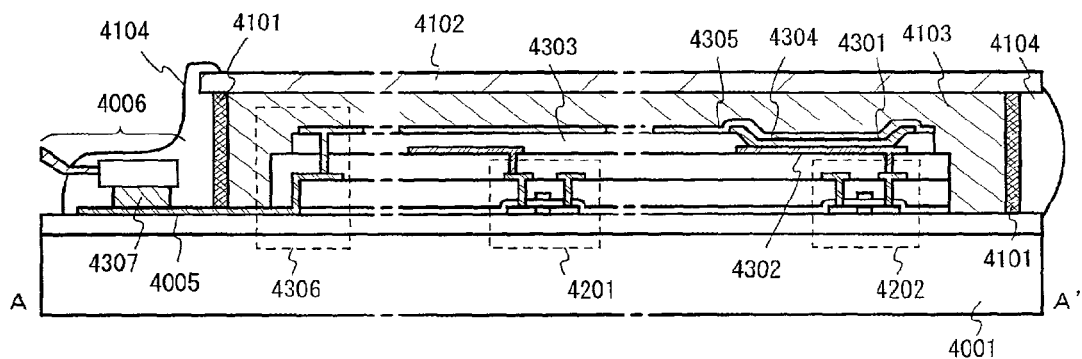

In FIGS. 14A and 14B, 4001 is a substrate, 4002 a pixel part, 4003 a drive circuit on the source side, 4004 a drive circuit of gate side, with each drive circuit going through the wire 4005 to FPC (flexible print circuit) 4006, where they are connected with external equipment.

At this moment, The first sealing material 4101, the covering material 4102, the loading material 4103 and the second sealing material 4104 are installed so as to surround the pixel part 4002, the drive circuit on the source side 4003 and the drive circuit on the gate side 4004.

FIG. 14B is the sectional view of the FIG. 14A cut at A-A', in which a photodiode 4201 as well as a TFT for driving EL (TFT to control the current to the EL element) contained in the pixel part are formed on the substrate 4001.

For the TFT 4202 for driving EL, a P-channel type TFT that is fabricated by a well-known method is used. And to the pixel part 4002, a holding capacitance (not illustrated) connected to the gate of TFT 4202 for driving EL is installed.

On the photodiode 4201 and the TFT 4202 for driving EL, an interlayer insulating film (planarization film) 4301 is formed and then a pixel electrode (anode) 4302 is formed on it in order to connect electrically with the drain of TFT 4202 for driving EL. For the pixel electrode 4302, a transparent conductive film with a high work function should be used. For the transparent conductive film, the compound of indium oxide and tin oxide, a compound of indium oxide and zinc oxide, zinc oxide, tin oxide, or indium oxide can be used. Furthermore, the above-mentioned transparent film to which gallium is added can also be used.

Then, the insulating film 4303 is formed on the pixel electrode 4302 and in this insulating film 4303 an opening is formed on the pixel electrode 4302. At this opening, the EL (electro-luminescence) layer 4304 is formed on the pixel electrode 4302. The EL layer 4304 can be made with a well known organic EL material or inorganic EL material. Furthermore, for the organic EL material, while there are low-molecular series (monomer series) materials and high-molecular series (polymer series) materials. both of them can be used.

For the fabrication method of EL layer 4304, a well-known vapor evaporation technique or method of application technique can be used. And for the structure of the EL layer, the hole injection layer, the hole transport layer, the light emission layer, the electron transport layer or the electron injection layer can be used in any combination to form a laminated structure or single layer structure.

On the EL layer 4304 is formed the cathode 4305 consisting of a conductive film having light blocking effect (typically conductive film mainly composed of aluminum, copper or silver, or a film laminated with them and other conductive film). Furthermore, it is preferable to eliminate as much as possible the humidity and oxygen which are at the interface between the cathode 4305 and the EL layer 4304. Therefore, a workmanship is required to continuously deposit both films in a vacuum, otherwise to form EL layer 4303 in nitrogen or rare gas atmosphere and then form the cathode 4305 without coming into contact with the oxygen or humidity. In this embodiment, the above-mentioned film deposition becomes possible by using a film deposition system of multi-chamber type (cluster tool type).

Then, the electrode 4305 is electrically connected with the wire 4005 in the region shown by 4306. The wire 4005 is to supply the prescribed voltage to the electrode 4305 and is connected electrically to the FPC 4006 via the anisotropic conductive film 4307.

As mentioned above, the EL element is formed consisting of the pixel electrode (anode) 4302, the EL layer 4304 and the cathode 4305. This EL element is surrounded by the covering material 4102, which is laminated to the substrate 4001 by the first sealing material 4101 and the first sealing material 4101, and encapsulated with the loading material 4103.

As the covering material 4102, the glass, metals (typically stainless material), ceramics, plastics (including plastic films) can be used. As the plastic material, FRP (Fiberglass Reinforced Plastics) plate, PVF (polyvinyl fluoride) film, Mylar film, polyester film or acrylic resin film can be used. Furthermore, a sheet composed of the aluminum foil inserted between the PVF films or Mylar films can be used as well.

However, if the radiation of the light from the EL element is directed to the covering material side, the covering material must be transparent. In such a case, a transparent substance like a glass plate, plastic plate, polyester film or acrylic film should be used.

For the loading material 4103, the ultraviolet curing resin or thermal curing resin can be used, and also PVC (polyvinyl chloride), acrylic, polyimide, epoxy resin, silicone resin, PVB (polyvinyl butyral), or EVA (ethylene-vinyl acetate) can be used. If a hygroscopic substance (preferably barium oxide) or other oxygen absorbent is put in the interior of this loading material 4103, the degradation of EL element can be prevented.

Furthermore, it is possible to put a spacer in the loading material 4103. In this case, the spacer can be formed with barium oxide to make the spacer itself hygroscopic. Furthermore, if the spacer is installed, it will be effective to provide a resin film on the cathode 4305 as a buffer layer in order to reduce the pressure from the spacer.

Then the wire 4005 is connected electrically to FPC 4006 via the anisotropic conductive film 4307. The wire 4005 transmits to FPC 4006 the signals, which are sent to the pixel part 4002, the drive circuit on the source side 4003 and the drive circuit on the gate side 4004 and then connected electrically with external equipment via FPC 4006.

Furthermore, in this embodiment the second sealing material 4104 is provided so as to cover the exposed part of the first sealing material 4101 and a part of FPC 4006 in order to achieve a structure which permits to shut out completely the outside air from the EL element. The EL display having the sectional view of FIG. 14B is s obtained in this way.

[Embodiment 8]

Figure 15A:
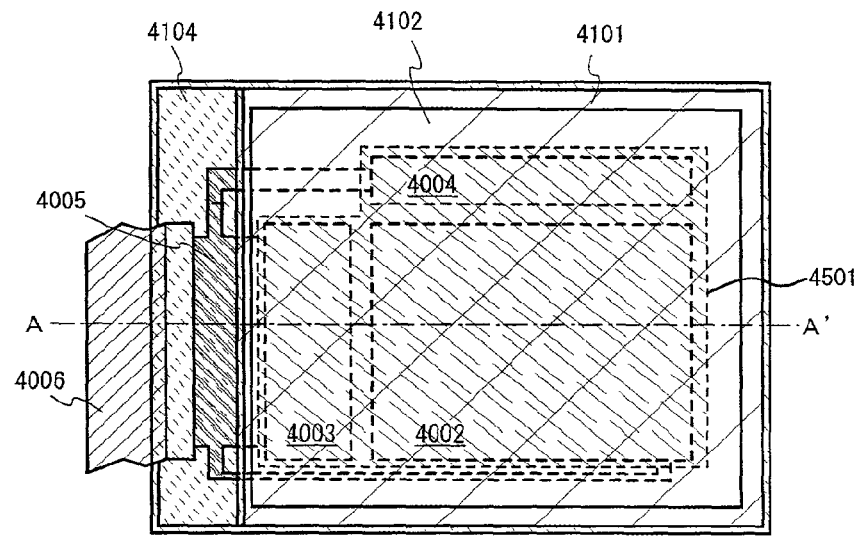
FIGS. 15A and 15B are an external view and a sectional view of the sensor-incorporated display, respectively.
Figure 15B:
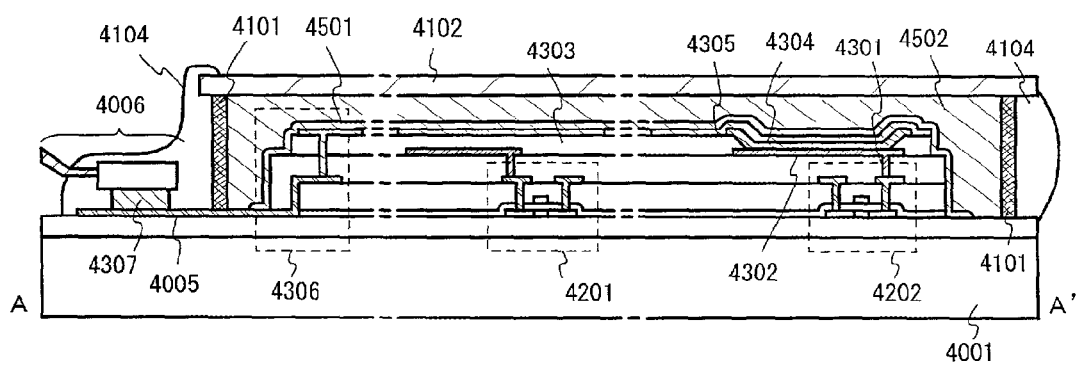
Figure 16:
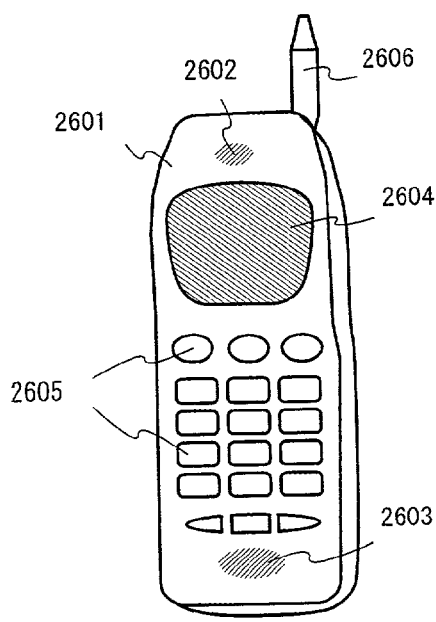
FIG. 16 is a drawing of a conventional portable telephone.
Figure 17:
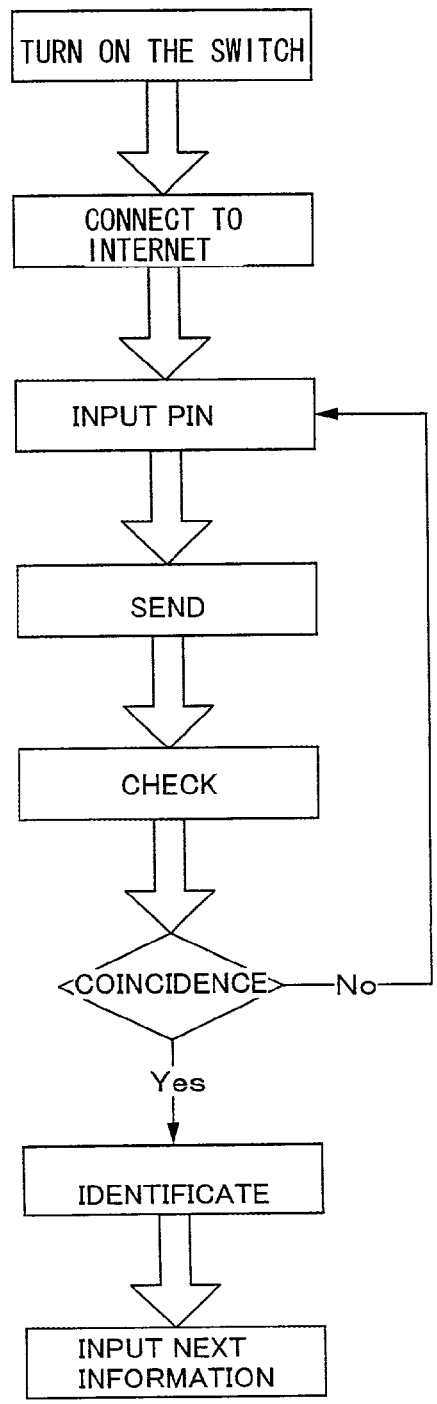
FIG. 17 is a flow of conventional identification of an individual.

This embodiment describes an example different from FIGS. 14A and 14B concerning the EL (electro-luminescence) display. Now, FIG. 15A is the top view the EL display of this invention and FIG. 15B is the sectional view of the EL display of this invention. But for the parts, which have been already shown in FIGS. 14A and 14B, the same codes will be utilized.

In FIGS. 15A and 15B, 4501 is a covering layer and it is formed on the substrate 4001 so as to cover the pixel part 4002, the drive circuit on the source side 4003 and is the drive circuit on the gate side 4004.

FIG. 15B corresponds to the sectional view of FIG. 15A cut at A-A', in which the interlayer insulating film 4301 made of resin material is formed on the photodiode 4201 and the TFT 4202 for driving EL, and then the pixel electrode (anode) 4302 is formed on it to connect electrically with the drain of TFT 4202 for driving EL.

Then, the insulating film 4303 is formed on the pixel electrode 4302, and an opening is formed in the insulating film 4303 on the pixel electrode 4302. In this opening, the EL (electro-luminescence) layer 4304 is formed on the pixel electrode 4302. For the EL layer 4304 a well-known organic EL material or inorganic EL material can be used. Furthermore, as the organic EL material, while there are low-molecular series (monomer series) materials and high-molecular series (polymer series) materials, both of them can be used.

As the fabrication method of EL layer 4304, a well-known vapor deposition technique or method of application technique can be used. And for the structure of EL layer, the hole injection layer, hole transport layer, light emission layer, electron transport layer or electron injection layer can be used in any combination to form a laminated structure or single layer structure.

On the EL layer 4304 is formed the cathode 4305 consisting of a conductive film having light blocking effect (typically conductive film with aluminum, copper or to silver as the main component, or laminated film with them and other conductive film). Furthermore, it is preferable to eliminate as much as possible the humidity and oxygen which are at the interface between the cathode 4305 and the EL layer 4304. Therefore, workmanship is required to continuously deposit both films in a vacuum, otherwise to form EL layer 4303 in nitrogen or rare gas atmosphere and then form the cathode 4305 without coming into contact with the oxygen or humidity. In this embodiment, the above-mentioned film deposition becomes possible by using a film deposition system of multi-chamber type (cluster tool type).

In this embodiment, a barrier layer 4501 is formed on the cathode 4305. As the barrier layer 4501 in this embodiment, The DLC (Diamond like carbon) film with addition of Si was used, but this embodiment is not limited to this. Besides the DLC film with addition of Si, a tantalum oxide, silicon nitride, aluminum nitride, silicon carbide or DLC film can also be used.

Since an EL layer has a weakness to the heat, the cathode and the barrier layer are preferable to be formed at as low a temperature as possible (more preferably between room temperature and 120° C.). While in this embodiment the barrier layer 4501 is formed in the plasma CVD method at a room temperature, it is also possible in the sputtering method. By forming the barrier layer in the plasma CVD method, it is possible to form continuously the EL layer, the cathode, and the barrier layer in the multi-chamber. The thickness of barrier layer is preferably of 10 to 100 nm and, in this embodiment, the barrier layer 4501 was formed at a thickness of 50 nm.

After the barrier layer formation 4501, a cover layer 4502 consisting of organic resin is formed on the barrier 4501. Furthermore, after having solved the organic resin in the solvent and having prepared the organic resin solution to an appropriate viscosity, it is positioned in the material chamber and applied in accordance with the electrolytic application method to form the covering layer 4502. At this moment, the viscosity of the organic resin solution is preferred to be of $1 \times 10^{-3}$ to $3 \times 10^{-2}$ Pa·s.

Further at this moment, by adding a hygroscopic agent or antioxidant agent such as barium oxide in the interior of the organic resin solution to form a cover layer, the humidity and oxygen which promote the degradation of EL layer can be prevented is from introducing into the EL layer.

Then, the cathode 4305 is connected electrically with the wire 4005 in the region shown by 4306. The wire 4005 is to supply the prescribed voltage to the cathode 4305 and is connected electrically to the FPC 4006 via the anisotropic conductive film 4307.

For the covering material 4102, the glass, metals (typically stainless material), ceramics and plastics (including plastic film) can be used. As for the plastic material, FRP (Fiberglass-Reinforced Plastics) plate, PVF (polyvinyl fluoride) film, Mylar film. polyester film or acrylic resin film can be used. Furthermore, a sheet composed of the aluminum foil inserted between the PVF films or Mylar films can be used as well.

However, if the light coming from EL element is radiated in the direction of the covering material, the covering material must be transparent. In such a case, a transparent substance such as glass plate, plastic plate, polyester film or acrylic film should be used.

Furthermore, it is possible to put a spacer in the covering layer 4502. At this time, by forming the spacer with barium oxide, it is possible to give a hygroscopicity to the spacer itself. Besides, in the case where a spacer is installed, it is effective to provide a resin film on the cathode 4305 as a buffer layer in order to reduce the pressure from the spacer.

Furthermore, the wire 4005 is electrically connected with FPC 4006 via the anisotropic conductive film 4307. The wire 4005 transmits to FPC 4006 the signals that are sent to the pixel part 4002, the drive circuit on the source side 4003 and the drive circuit on the gate side 4004, and then connected electrically to external equipment by FPC 4006.

Besides, in this embodiment, the second sealing material 4104 is provided so as to cover the exposed part of the first sealing material 4101 and a part of FPC 4006 in order to get a structure permitting to shut out completely the outside air from the EL element. By these, the EL display having the sectional view of FIG. 15B is achieved.

The portable communication device of this invention is possible to identify an individual by means of the functions of the sensor incorporated in the device and has a possibility to have a high reliability and simplicity, compared with the conventional identification works consisting of entering a numerical value (personal identification number).

What is claimed is:
1. A portable information device comprising:
a display portion configured to read biological information of a user; and
a circuit portion configured to identify the user by checking the biological information,
wherein the display portion comprises a semiconductor layer and a metal layer over the semiconductor layer, wherein the semiconductor layer includes a first impurity region and a second impurity region, wherein a first edge of the metal layer is aligned with an edge of the first impurity region, and wherein a second edge of the metal layer is aligned with an edge of the second impurity region.

2. The portable information device according to claim 1, wherein the semiconductor layer is included in a photodiode of the display portion.

3. The portable information device according to claim 1,
wherein the display portion further comprises a reset transistor, and
wherein the reset transistor is electrically connected to one of the first impurity region and the second impurity region.

4. The portable information device according to claim 1, wherein the biological information is a fingerprint.

5. The portable information device according to claim 1, wherein the biological information is a palm pattern.

6. The portable information device according to claim 1, wherein the display portion comprises an organic EL display.

7. The portable information device according to claim 6,
wherein the organic EL display comprises a first substrate and a second substrate over the first substrate,
wherein a first sealing material is provided between the first substrate and the second substrate, and
wherein a second sealing material is provided outside the first sealing material.

8. The portable information device according to claim 2, further comprising an operating key configured to start to read the biological information of the user.

9. The portable information device according to claim 8, wherein the operating key is provided on a side of the portable information device.

10. A portable information device comprising:
a display portion configured to read biological information of a user;
a circuit portion configured to identify the user by checking the biological information; and
an antenna configured to transmit an identification information of the user,
wherein the display portion comprises a semiconductor layer and a metal layer over the semiconductor layer,
wherein the semiconductor layer includes a first impurity region and a second impurity region,
wherein a first edge of the metal layer is aligned with an edge of the first impurity region, and
wherein a second edge of the metal layer is aligned with an edge of the second impurity region.

11. The portable information device according to claim 10, wherein the semiconductor layer is included in a photodiode of the display portion.

12. The portable information device according to claim 10,
wherein the display portion further comprises a reset transistor, and
wherein the reset transistor is electrically connected to one of the first impurity region and the second impurity region.

13. The portable information device according to claim 10, wherein the biological information is a fingerprint.

14. The portable information device according to claim 10, wherein the biological information is a palm pattern.

15. The portable information device according to claim 10, wherein the display portion comprises an organic EL display.

16. The portable information device according to claim 15,
wherein the organic EL display comprises a first substrate and a second substrate over the first substrate,
wherein a first sealing material is provided between the first substrate and the second substrate, and
wherein a second sealing material is provided outside the first sealing material.

17. The portable information device according to claim 10, further comprising an operating key configured to start to read the biological information of the user.

18. The portable information device according to claim 17, wherein the operating key is provided on a side of the portable information device.

* * * * *

UNITED STATES PATENT AND TRADEMARK OFFICE
CERTIFICATE OF CORRECTION

PATENT NO. : 9,008,377 B2  
APPLICATION NO. : 14/339510  
DATED : April 14, 2015  
INVENTOR(S) : Shunpei Yamazaki, Jun Koyama and Yu Yamazaki Page 1 of 1

It is certified that error appears in the above-identified patent and that said Letters Patent is hereby corrected as shown below:

In the specification

Column 2, line 13, after "individual" insert --,--;

Column 2, line 21, before "comprising:" delete "s";

Column 6, line 14, after "Internet" replace "." with --,--;

Column 10, line 65, after "Ltd." insert --,--:

Column 11, line 41, replace "fondled" with --formed--;

Column 14, line 17, after "each" delete "to";

Column 14, line 17, after "region" delete "to";

Column 15, line 24, after "pixel" delete "is";

Column 16, line 18, after "denotes" delete "to";

Column 17, line 67, after "materials" replace "." with --,--;

Column 19, line 3, after "is" delete "s";

Column 19, line 14, after "and" delete "is";

Column 19, line 40, after "or" delete "to";

Column 20, line 17, after "prevented" delete "is";

Column 20, line 27, after "film" replace "." with --,--; and

In the claims

Column 21, line 29, in claim 8, after "claim" replace "2" with --1--.

Signed and Sealed this  
Fifth Day of January, 2016

Michelle K. Lee  
*Director of the United States Patent and Trademark Office*